(12) United States Patent
Brandan et al.

(10) Patent No.: US 8,771,692 B2
(45) Date of Patent: Jul. 8, 2014

(54) METHODS FOR TREATMENT OF MUSCULAR DYSTROPHY

(75) Inventors: Enrique Brandan, Santiago (CL); Roel Goldschmeding, Bilthoven (NL); Noelynn A. Oliver, Los Altos, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 13/380,489

(22) PCT Filed: Jul. 2, 2010

(86) PCT No.: PCT/US2010/001899
§ 371 (c)(1),
(2), (4) Date: Mar. 14, 2012

(87) PCT Pub. No.: WO2011/002525
PCT Pub. Date: Jan. 6, 2011

(65) Prior Publication Data
US 2012/0164151 A1    Jun. 28, 2012

Related U.S. Application Data

(60) Provisional application No. 61/270,047, filed on Jul. 2, 2009.

(51) Int. Cl.
*A61K 39/395* (2006.01)
*C07K 16/22* (2006.01)
*A61K 39/00* (2006.01)

(52) U.S. Cl.
CPC ........... *C07K 16/22* (2013.01); *A61K 2039/505* (2013.01)
USPC .................... 424/139.1; 424/141.1; 424/145.1

(58) Field of Classification Search
None
See application file for complete search history.

(56) References Cited

U.S. PATENT DOCUMENTS

2004/0248206 A1*  12/2004  Lin et al. .......................... 435/7.1
2005/0282737 A1*  12/2005  Burchardt ......................... 514/2

OTHER PUBLICATIONS

Cohn et al., Nature Medicine, 13(2);204-210, 2007.*
Leask, Frontiers in Bioscience (Elite Edition), 1:115-122, Jun. 1, 2009.*
Droppelmann et al., J. Biol. Chem. May 2009, 284:13551-13561, published online Mar. 9, 2009.*
Sun, G., et al., "Connective Tissue Growth Factor is Overexpressed in Muscles of Human Muscular Dystrophy," J. Neurol. Sci. (2008) 267:48-56.
Whitehead, N. P., et al., "Muscle Damage in mdx (Dystrophic) Mice: Role of Calcium and Reactive Oxygen Soecies," Clin. Exp. Pharmacol. Physiol. (2006) 33:657-662.
Willmann, R., et al., "Mammalian Animal Models for Duchenne Muscular Dystrophy," Neuromuscul. Disord. (2009) 19:241-249. (Abstract).
Bernasconi P., et al., "Transforming Growth Factor-Beta1 and Fibrosis in Congenital Muscular Dystrophies," Neuromuscul. Disord. (1999) 9:28-33. (Abstract).
Cohn, Ronald, D., et al., "Angiotensin II Type 1 ReceptorBlockade Attenuates TGF-Beta-Induced Failure of Muscle Regeneration in Multiple Myopathic States," Nature Med. (2007) 13:204-210.
Fukushima, K., et al., "The Use of an Antifibrosis Agent to Improve Muscle Recovery After Laceration," Am. J. Sports Med. (2001) 29:394-402. (Abstract).
Hartel, J.V., et al., "Impact of Prednisone on TGF-Beta1and Collagen in Diaphragm Muscle From mdx Mice," Muscle Nerve. (2001) 24:428-432. (Abstract).
Leask, A., "Signaling in Fibrosis: Targeting the TGF Beta, Endothelin-1 and CCN2 Axis in Scleroderma," Front Biosci (Elite Ed). (2009) 1:115-122. (Abstract).
Noirez, P., et al. "CTGF Expression in Normal and Dystrophic Muscles: Correlation to Fibrosis," (2007). (Abstract).
Passerini, L., et al., "Fibrogenic Cytokines and Extent of Fibrosis in Muscle of Dogs with X-Linked Golden Retriever Muscular Dystrophy," Nueromuscul. Disord. (2002) 12:828-835.
Porter, J.D., et al., "Dissection of Temporal Gene Expression Signatures of Affected and Spared Muscle Groups in Dystrophin-Deficient (mdx) Mice," Hum. Mol. Genet. (2003) 12:1813-1821.
Porter, J.D., et al., "Temporal Gene Expression Profiling of Dystrophin-Deficient (mdx) Mouse Diaphragm Identified Conserved and Muscle Group-Specific Mechanisms in the Pathogenesis of Muscular Dystrophy," Hum. Mol. Genet. (2004) 13:257-269.
Shi-Wen, X., et al., "Regulation and Function of Connective Tissue Growth Factor/CCN2 in Tissue Repair, Scarring and Fibrosis," Cytokine Growht Factor Rev. (2008) 19:133-144.

* cited by examiner

*Primary Examiner* — Marianne P Allen
(74) *Attorney, Agent, or Firm* — Jeanne C. Price, Esq.; Paul Borchardt

(57) ABSTRACT

The present invention relates to methods and agents useful for treating muscular dystrophy. Methods and agents for treating various physiological and pathological features associated with muscular dystrophy are also provided.

12 Claims, 14 Drawing Sheets

METHODS FOR TREATMENT OF MUSCULAR DYSTROPHY

This application claims the benefit of U.S. Provisional Application Ser. No. 61/270,047, filed on 2 Jul. 2009, which is incorporated by reference herein it its entirety.

FIELD OF THE INVENTION

The present invention relates to methods and agents useful for treating muscular dystrophy. Methods and agents for treating various physiological and pathological features associated with muscular dystrophy are also provided.

BACKGROUND

Muscular dystrophy refers to a group of more than 30 hereditary muscle diseases characterized by progressive skeletal muscle weakness, degeneration of skeletal muscle fibers, defects in certain muscle proteins, and death of muscle cells and tissue. As muscular dystrophy progresses and muscles weaken, fixations (contractures) can develop in joints, in which muscles and tendons shorten, restricting the flexibility and mobility of joints and muscles. Muscular dystrophies are multi-system disorders with manifestations in numerous body systems including the heart, gastrointestinal and nervous systems, endocrine glands, skin, eyes, and other organs.

Duchenne muscular dystrophy is the most common childhood form of muscular dystrophy, affecting about 1 out of every 3500 males. Duchenne muscular dystrophy is characterized by a near complete lack of dystrophin protein production, which most often is caused by mutations in the gene coding for dystrophin. Signs and symptoms of Duchenne muscular dystrophy usually appear between the ages of 2 and 6, first affecting the muscles of the pelvis, upper arms, and upper legs. By late childhood, most children with Duchenne muscular dystrophy are unable to walk and most die in their late teens or early 20s, often from respiratory muscle weakness or cardiac complications. Other forms of muscular dystrophy include Becker's muscular dystrophy, a less severe form of Duchenne muscular dystrophy in which a partially functional (i.e., truncated) form of dystrophin is produced, congenital muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

There is currently no cure for any form of muscular dystrophy. Respiratory therapy, physical therapy to prevent contractures and maintain muscle tone, use of orthopedic appliances for support, and corrective orthopedic surgery are often used to improve quality of life. Current therapeutic approaches to muscular dystrophies involve administration of steroids (e.g., glucocorticoids, corticosteroioids), such as, for example, prednisone or deflazacort. These treatments result in modest benefits and are often accompanied by undesirable side effects, including, for example, osteoporosis, hypertension, and weight gain. Thus, there is a need in the art for methods and agents useful for effectively treating muscular dystrophy, for reducing the progression and severity of muscular dystrophy, and for preventing or treating one or more symptoms of muscular dystrophy.

The present invention meets this need by providing novel methods and agents for use in treating muscular dystrophy. In particular, the present invention provides methods and agents for the treatment of muscular dystrophy by inhibiting connective tissue growth factor (CTGF) activity or expression.

SUMMARY OF THE INVENTION

In one aspect, the present invention provides a method for treating muscular dystrophy in a subject having muscular dystrophy, the method comprising administering to the subject a therapeutically effective amount of an agent that inhibits CTGF, thereby treating muscular dystrophy in the subject. In some embodiments, the muscular dystrophy is selected from the group consisting of Becker muscular dystrophy, Congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

The subject is an individual, preferably a mammal, more preferably a human, who has muscular dystrophy.

In another aspect, the present invention provides a method for preventing, reducing, or treating a clinical symptom of muscular dystrophy in a subject having muscular dystrophy, the method comprising administering to the subject a therapeutically effective amount of an agent that inhibits CTGF, thereby preventing, reducing, or treating a clinical symptom of muscular dystrophy in the subject. In some embodiments, the clinical symptom of muscular dystrophy is muscle damage, muscle wasting, muscle degeneration, or muscle atrophy. In specific embodiments, the muscle damage is skeletal muscle damage, the muscle wasting is skeletal muscle wasting, the muscle degeneration is skeletal muscle degeneration, and the muscle atrophy is skeletal muscle atrophy.

In another embodiment, the present invention provides a method for treating, reducing, or preventing the progression of muscular dystrophy in a subject having muscular dystrophy, the method comprising administering to the subject a therapeutically effective amount of an agent that inhibits CTGF. In certain embodiments, the present invention provides a method for treating, reducing, or preventing the progression of muscle degeneration or joint contractures in a subject having muscular dystrophy, the method comprising administering to the subject a therapeutically effective amount of an agent that inhibits CTGF.

In one embodiment, the present invention provides a method for reducing serum creatine kinase levels in a subject having muscular dystrophy, the method comprising administering to the subject a therapeutically effective amount of an agent that inhibits CTGF, thereby reducing serum creatine kinase levels in the subject. In other embodiments, the present invention provides a method for reducing muscle damage in a subject having muscular dystrophy, the method comprising administering to the subject a therapeutically effective amount of an agent that inhibits CTGF, thereby reducing muscle damage in the subject. In certain embodiments, the muscle damage is skeletal muscle damage.

In another aspect, the present invention provides a method for reducing or preventing muscle fibrosis in a subject having muscular dystrophy, the method comprising administering to the subject a therapeutically effective amount of an agent that inhibits CTGF, thereby reducing or preventing muscle fibrosis in the subject. In certain embodiments, the method of the present invention reduces or prevents skeletal muscle fibrosis in a subject having muscular dystrophy by administering to the subject a therapeutically effective amount of an agent that inhibits CTGF.

In one embodiment, the present invention provides a method for improving muscle function in a subject having muscular dystrophy, the method comprising administering to the subject a therapeutically effective amount of an agent that inhibits CTGF. In another embodiment, the present invention provides methods for treating, preventing, or reducing a decrease in muscle mass, muscle size, or absolute muscle strength in a subject having muscular dystrophy, the method comprising administering to the subject a therapeutically effective amount of an agent that inhibits CTGF. In yet another embodiment, the present invention provides methods for treating, preventing, or reducing weight loss in a subject having muscular dystrophy, the method comprising administering to the subject a therapeutically effective amount of an agent that inhibits CTGF.

In one aspect, the present invention provides a method for treating, preventing or reducing exercise-induced muscle damage in a subject having muscular dystrophy, the method comprising administering to the subject a therapeutically effective amount of an agent that inhibits CTGF, thereby treating, preventing or reducing exercise-induced muscle damage in the subject. In certain aspects, the present invention provides a method for treating, preventing or reducing exercise-induced skeletal muscle damage in a subject having muscular dystrophy, the method comprising administering to the subject a therapeutically effective amount of an agent that inhibits CTGF.

In another embodiment, the present invention provides methods for improving or increasing muscle regeneration in a subject having muscular dystrophy, the method comprising administering to the subject a therapeutically effective amount of an agent that inhibits CTGF. In certain embodiments, the present invention provides methods for improving or increasing skeletal muscle regeneration in a subject having muscular dystrophy, the method comprising administering to the subject a therapeutically effective amount of an agent that inhibits CTGF. In yet another embodiment, the present invention provides methods for improving or increasing muscle repair in a subject having muscular dystrophy, the method comprising administering to the subject a therapeutically effective amount of an agent that inhibits CTGF. In particular embodiments, the present invention provides methods for improving or increasing skeletal muscle repair in a subject having muscular dystrophy, the method comprising administering to the subject a therapeutically effective amount of an agent that inhibits CTGF.

In other embodiments, the present invention provides a method for reducing extracellular matrix protein levels in muscle in a subject having muscular dystrophy, the method comprising administering to the subject a therapeutically effective amount of an agent that inhibits CTGF, thereby reducing extracellular matrix protein levels in the subject. In certain aspects of the present embodiment, the muscle is skeletal muscle. In other aspects, the extracellular matrix protein is periostin, fibronectin, α-SMA, thrombospondin-1, decorin, or type III collagen. In another embodiment, the present invention provides a method for reducing necrosis of muscle fiber in a subject having muscular dystrophy, the method comprising administering to the subject a therapeutically effective amount of an agent that inhibits CTGF. In particular embodiments, the present invention provides a method for reducing necrosis of skeletal muscle fiber in a subject having muscular dystrophy, the method comprising administering to the subject a therapeutically effective amount of an agent that inhibits CTGF.

In one embodiment, the present invention provides a method for increasing myotube formation, myotube survival, muscle cell differentiation, or muscle cell survival in a subject having muscular dystrophy, the method comprising administering to the subject a therapeutically effective amount of an agent that inhibits CTGF. In one aspect the muscle cell is a myoblast, a satellite cell, a skeletal muscle cell, a cardiac muscle cell, or a smooth muscle cell. In another embodiment, the present invention provides a method for increasing expression of a myogenic factor, the method comprising administering to the subject a therapeutically effective amount of an agent that inhibits CTGF. In certain embodiments, the myogenic factor is selected from the group consisting of myogenin, desmin, MyoD, Myf5, MRF4 (Myf6), MCF2, and myosin. In yet another embodiment, the present invention provides a method for increasing activation or differentiation of myoblasts in a subject having muscular dystrophy, the method comprising administering to the subject a therapeutically effective amount of an agent that inhibits CTGF.

These and other methods of the invention are accomplished by administering an anti-CTGF agent to the subject having muscular dystrophy. In particular embodiments the anti-CTGF agent is an anti-CTGF antibody, a polynucleotide inhibitor of CTGF expression (for example, an antisense oligonucleotide, siRNA, shRNA, miRNA, or ribozyme) or a small molecule inhibitor of CTGF activity. In a preferred embodiment, the anti-CTGF agent is an anti-CTGF antibody. A preferred anti-CTGF antibody is CLN1 or mAb1 as described in U.S. Pat. No. 7,405,274. In one embodiment, the agent is useful for manufacturing a medicament for treating muscular dystrophy, wherein the agent inhibits CTGF. In certain embodiments, the agent that inhibits CTGF is used in combination with an angiotensin converting enzyme inhibitor (ACEi), an angiotensin receptor blocker (ARB), a statin, a calcium channel blocker, a beta-blocker, a glucocorticoid, a corticosteroid, an advanced glycation endproduct (AGE) inhibitor, or a diuretic.

These and other embodiments of the present invention will readily occur to those of skill in the art in light of the disclosure herein, and all such embodiments are specifically contemplated.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise.

DESCRIPTION OF THE INVENTION

Figure 1A:
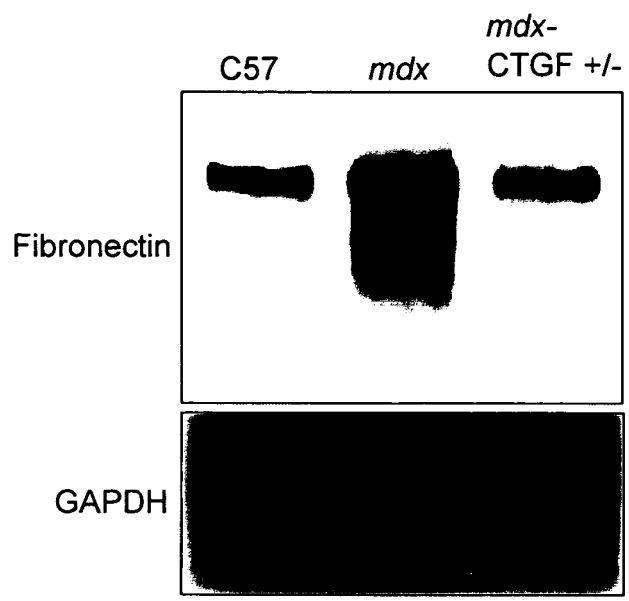
FIGS. 1A and 1B set forth data showing methods and agents of the present invention reduced fibronectin levels in dystrophic skeletal muscle in an animal model of muscular dystrophy.

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the present invention. Nothing herein is to be construed as an admission that the present invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention is based, in part, on the discovery of unexpected benefits of inhibition of connective tissue growth factor (CTGF) in treatment of muscular dystrophy. The present invention sets forth evidence that inhibition of CTGF provides a therapeutic approach to treat or ameliorate various physiological and pathological aspects of muscular dystrophy. For example, the present invention provides data demonstrating that reduced expression of CTGF attenuated various pathological features of muscular dystrophy, such as, for example, reduced skeletal muscle fibrosis and reduced skeletal muscle extracellular matrix protein levels, in an animal model of Duchenne muscular dystrophy.

The present invention provides methods and agents for preventing, reducing, or treating one or more clinical symptoms of muscular dystrophy. In certain embodiments, the present invention provides methods for preventing, reducing, or treating muscle damage, muscle wasting, muscle degeneration, or muscle atrophy by inhibiting CTGF in a subject having muscular dystrophy. In other embodiments, the subject having muscular dystrophy is an animal, more preferably a mammal, and most preferably a human.

In certain embodiments, the treatment of muscular dystrophy by inhibiting CTGF, as provided by the methods and agents of the present invention, results in preserved muscle function, prevention of joint contractures, improvement in quality of life, and a reduction in the progression of muscle degeneration in a subject having muscular dystrophy.

The present invention also provides agents for use in the methods described herein. Such agents (i.e., such anti-CTGF agents) inhibit CTGF activity or expression, and may include small molecule compounds; peptides and proteins including antibodies or functionally active fragments thereof; and polynucleotides including small interfering ribonucleic acids (siRNAs), micro-RNAs (miRNAs), ribozymes, and antisense sequences. (See, e.g., Zeng (2003) Proc Natl Acad Sci USA 100:9779-9784; and Kurreck (2003) Eur J Biochem 270:1628-1644.) The present invention also provides agents for use in manufacturing a medicament for treating muscular dystrophy, wherein the agent inhibits CTGF.

The section headings are used herein for organizational purposes only, and are not to be construed as in any way limiting the subject matter described herein.

Methods

The present invention relates, in part, to the discovery that inhibition or reduction of CTGF activity or expression in a subject is effective at treating muscular dystrophy in a subject having muscular dystrophy. Accordingly, the present invention provides methods for treating muscular dystrophy in a subject having muscular dystrophy, the method comprising administering to the subject an effective amount of an agent that inhibits CTGF, thereby treating muscular dystrophy in the subject. As used herein, an agent that inhibits CTGF (i.e., an anti-CTGF agent) is an agent that inhibits the expression or activity of CTGF.

Muscular dystrophies are associated with various clinical symptoms, including muscle damage, muscle wasting, muscle weakness, muscle degeneration, muscle atrophy, weight loss, and elevated serum creatine kinase levels. The present invention provides methods for preventing, reducing, or treating a clinical symptom of muscular dystrophy in a subject having muscular dystrophy, the method comprising administering to the subject an effective amount of an agent that inhibits CTGF, thereby preventing reducing, or treating the clinical symptom in the subject. Improvement in any one clinical symptom associated with muscular dystrophy by administering an effective amount of an agent that inhibits CTGF is specifically provided by the present invention.

Subjects with muscular dystrophy develop skeletal muscle fibrosis, characterized by excessive connective tissue and extracellular matrix protein deposition in their muscles. The present invention shows that reduced expression of CTGF resulted in reduced skeletal muscle fibrosis in an animal model of muscular dystrophy. (See, e.g., Example 1.) Thus, the present invention provides methods useful for treating or reducing muscle fibrosis associated with muscular dystrophy. In some embodiments, the present invention provides methods for treating or reducing muscle fibrosis in a subject having muscular dystrophy, the method comprising administering to the subject an effective amount of an agent that inhibits CTGF, thereby treating or reducing muscle fibrosis. In certain embodiments, the muscle fibrosis is skeletal muscle fibrosis.

Periostin is an extracellular adhesive protein secreted by fibroblasts. Periostin expression is upregulated following injury to muscle and during remodeling processes in muscle, such as that which occurs in subjects with muscular dystrophy. Periostin is a regulator of fibrosis that affects the deposition and attachment of collagen to muscle fibers. (Oka et al. (2007) Circ Res. 101:313-321; Borg and Markwald (2007) Circ Res 101:230-231.) Increased periostin levels are associated with muscle fibrosis and scar formation. For example, increased expression of periostin in patients with heart failure and in animal models of cardiac remodeling has been observed. (Elsherif et al. Circ Res. (2008) 102:1109-17.) In animal studies in which periostin expression was knocked out, reduced fibrosis in response to muscle injury was observed. The results of these studies suggested that a reduction in periostin expression or activity could benefit a subject having muscle fibrosis or a muscle remodeling disease, such as, for example, that associated with muscular dystrophy.

The present invention shows that reduced CTGF expression resulted in reduced periostin levels in muscle in an animal model of Duchenne muscular dystrophy. (See, e.g., Example 1.) Therefore, the present invention provides methods and agents for reducing periostin levels in a subject having muscular dystrophy by inhibiting CTGF activity or expression. In certain embodiments, the methods of the present invention are effective at reducing periostin levels in a subject with muscular dystrophy by administering an effective amount of an agent that inhibits CTGF activity or expression. In certain embodiments, methods of the present invention are effective at reducing periostin levels in muscle, including, for example, in skeletal muscle, in smooth muscle, or in cardiac muscle, by inhibiting CTGF activity or expression by administering to the subject an effective amount of an agent that inhibits CTGF. Periostin expression is associated with muscle fibrosis and scar formation in subjects having muscular dystrophy; therefore, by reducing periostin expression by inhibition of CTGF, the present methods and agents are effective at treating muscular dystrophy.

Fibronectin is an extracellular matrix glycoprotein secreted by fibroblasts that is associated with increased fibrosis in muscles of patients with muscular dystrophy. Increased fibronectin levels in muscle are indicative of progressive muscle fibrosis. (Heling et al. (2000) Circ Res. 86:846-53.) The present invention shows that reduced CTGF expression resulted in reduced fibronectin levels in muscle in an animal model of Duchenne muscular dystrophy. (See, e.g., Example 1.) Therefore, the present invention provides methods and agents for reducing fibronectin levels in a subject having muscular dystrophy by inhibiting CTGF activity or expression. In certain embodiments, the methods of the present invention are effective at reducing fibronectin levels in a subject having muscular dystrophy by administering an agent that inhibits CTGF activity or expression. In other embodiments, methods and agents of the present invention are effective at reducing fibronectin levels in muscle, including, for example, in skeletal muscle, in smooth muscle, or in cardiac muscle, by inhibiting CTGF activity or expression.

In other embodiments, the present invention provides methods for reducing α-SMA, thrombospondin-1, decorin, and type III collagen in a subject having muscular dystrophy by inhibiting CTGF.

Muscular dystrophy is associated with impaired muscle (e.g., skeletal muscle) regeneration and repair. Skeletal muscle regeneration and repair involves the activation of specialized muscle progenitor cells, called satellite cells, which reside in muscle in a quiescent state. (Scime and Rudnicki (2006) Curr Opin Clin Nutr Metab Care. 9:214-9. ) Following skeletal muscle injury, satellite cells are activated, exit the quiescent state, and proliferate. In this proliferative stage, the proliferating satellite cells are referred to as myogenic precursor cells or myoblasts. (Le Grand and Rudnicki (2007) Curr Opin Cell Biol. 19:628-33. ) Myoblasts can be identified by their expression of specific myogenic regulatory factors MyoD and Myf5. During normal muscle differentiation and repair, myoblasts proliferate, migrate to the site of injury, and fuse into myofibers, thereby regenerating damaged or degenerating myofibers. (Seale and Rudnicki (2000) Dev Biol. 218:115-24. ) Differentiating myoblasts can be identified by their expression of the regulatory factors myogenin, MCF2, MRF4 (Myf6). In subjects having muscular dystrophy, however, normal muscle differentiation, regeneration, and repair are impaired, and muscle degeneration and wasting is observed.

The present invention provides methods and agents for improving skeletal muscle regeneration or skeletal muscle repair in a subject having muscular dystrophy by inhibiting CTGF.

The present invention provides methods and agents useful for increasing myoblast activation and myoblast differentiation. (See, e.g., Example 2. ) In some embodiments, the present invention provides methods for increasing myoblast activation and myoblast differentiation in a subject having muscular dystrophy by inhibiting CTGF. In other embodiments, the present invention provides methods for increasing myoblast activation and myoblast differentiation in a subject having muscular dystrophy, the method comprising administering to the subject an effective amount of an agent that inhibits CTGF. In yet other embodiments, the present invention provides methods for increasing MyoD and Myf5 expression in muscle in a subject having muscular dystrophy, the method comprising administering to the subject an effective amount of an agent that inhibits CTGF.

Differentiating myoblasts fuse together to form myotubes. The present invention provides methods and agents for increasing myotube formation in a subject having muscular dystrophy by inhibiting CTGF. In some embodiments, the present invention provides methods for increasing myogenin, MCF2, MRF4 (Myf6) expression in muscle, the method comprising administering to the subject an effective amount of an agent that inhibits CTGF.

As muscular dystrophy progresses, subjects with muscular dystrophy suffer from skeletal muscle weakness and impaired skeletal muscle function. Skeletal muscle weakness and skeletal muscle function can be assessed by various means, including measurement of maximal force and tetanus in skeletal muscle. The present invention shows that inhibition of CTGF results in increased maximal force and tetanus in skeletal muscle. (See, e.g., Example 5.) Therefore, the present invention provides methods and agents for improving skeletal muscle function, for reducing skeletal muscle weakness, and for increasing skeletal muscle strength in a subject with muscular dystrophy by inhibiting CTGF. In certain embodiments, the present invention provides methods for improving skeletal muscle function, for reducing skeletal muscle weakness, or for increasing skeletal muscle strength in a subject having muscular dystrophy, the method comprising administering to the subject an effective amount of an agent that inhibits CTGF, thereby improving skeletal muscle function, reducing skeletal muscle weakness, or increasing skeletal muscle strength in the subject In particular, the present invention demonstrates that inhibition of CTGF provides an effective treatment of the clinical symptoms of muscular dystrophy, such as, for example, an effective treatment for improving skeletal muscle function. In some embodiments, the clinical symptom of muscular dystrophy is muscle damage, muscle wasting, muscle weakness, muscle degeneration, muscle atrophy, or weight loss.

In other embodiments, the present invention provides methods and agents for treating or preventing a reduction in body weight, muscle mass, or muscle size in a subject having muscular dystrophy by inhibiting CTGF.

Elevated levels of serum creatine kinase are observed in subjects with muscular dystrophy. Elevated levels of serum creatine kinase are a symptom of muscle damage associated with or due to chronic disease or acute muscle injury. Serum creatine kinase may be measured by any technique available to one of skill in the art. The present invention shows that inhibition of CTGF resulted in reduced serum creatine kinase levels in an animal of muscular dystrophy. (See, e.g., Example 4.) In certain embodiments, the present invention provides methods for reducing serum creatine kinase levels in a subject having muscular dystrophy, the method comprising administering to the subject an effective amount of an agent that inhibits CTGF, thereby reducing serum creatine kinase levels. As elevated levels of serum creatine kinase are associated with muscle damage or injury, a reduction in serum creatine kinase levels is indicative of reduced muscle damage or injury. Therefore, in certain embodiments, the present invention provides methods for reducing muscle damage or injury in a subject having muscular dystrophy, the method comprising administering to the subject an effective amount of an agent that inhibits CTGF, thereby reducing muscle damage or injury in the subject.

Subjects

The present invention provides methods and agents for treating muscular dystrophy in a subject having muscular dystrophy by inhibiting CTGF. Muscular dystrophy refers to a group of muscle diseases having defects in muscle membrane or muscle proteins characterized, in part, by ongoing muscle degeneration and regeneration leading to progressive muscle weakness, increased susceptibility to muscle damage, and degeneration and death of muscle cells and tissues. The determination as to whether a subject has muscular dystrophy, as well as the determination of a particular type of muscular dystrophy, can be made by any measure accepted and utilized by those skilled in the art. Diagnosis of subjects with muscular dystrophy is generally contingent on a targeted medical history and examination, biochemical assessment, muscle biopsy, or genetic testing.

A subject's medical history may be used to diagnose muscular dystrophy. Subjects with Duchenne muscular dystrophy, for example, are symptomatic before the age of 5 years, and experience difficulty running, jumping, and climbing steps. Proximal weakness causes individuals to use their arms in rising from the floor (i.e. Gowers' sign). Independent ambulation is often lost by 14 years of age, with subsequent deterioration in respiratory function and development of contractures and scoliosis. (See, e.g., Darras (2006) Continuum. 12: 33-75. ) Static cognitive impairment is common. (Wicksell et al. (2004) Dev Med Child Neurol. 46:154-159. ) Approximately one third of boys with Duchenne muscular dystrophy develop cardiomyopathy by 14 years of age, and virtually all do after 18 years. Congestive heart failure and arrhythmias are common in end-stage Duchenne muscular dystrophy. (See, e.g., Kirchmann et al. (2005) Pediatr Cardiol. 26:66-72. ) Most young men with Duchenne muscular dystrophy die in their late teens or early twenties from respiratory insufficiency or cardiac failure.

Biochemical assessments, such as, for example, measurement of serum creatine kinase levels, may be used to diagnose a subject having muscular dystrophy. Increased serum creatine kinase levels indicate increased muscle damage. Before the age of 5 years, serum creatine kinase levels are 10 to 200 times higher in subjects with Duchenne muscular dystrophy and Becker muscular dystrophy compared to normal levels. (See, e.g., Cardamone et al. (2008) Semin Neurol. 28:250-9. ) Methods and agents of the present invention reduce serum creatine kinase levels in an animal model of muscular dystrophy. (See, e.g., Example 4. ) Thus, the present invention provides treatment of subjects having muscular dystrophy with high or elevated serum creatine kinase levels. In certain embodiments, a human subject suitable for treatment using the present methods, agents, and medicaments is a subject having muscular dystrophy with high or elevated serum creatine kinase levels, particularly when the subject has a condition as described herein.

Muscle biopsy may also be used to diagnose a subject as having muscular dystrophy. For example, muscle biopsy from Duchenne muscular dystrophy patients shows degeneration, regeneration, and variability of fiber size with replacement of muscle by fat and connective tissue. Muscle immunohistochemical studies with anti-dystrophin antibodies shows complete absence of staining in muscle from subjects with Duchenne muscular dystrophy and reduced staining in muscle from subject with Becker muscular dystrophy. (Cardamone et al. (2008) Semin Neurol. 28:250-9. ) The present invention provides methods and agents for treatment of muscular dystrophy in a subject with reduced or low muscle dystrophin levels.

Genetic testing may also be employed to diagnose a subject as having muscular dystrophy. Techniques used in genetic testing include the polymerase chain reaction (PCR), Southern blotting, mutation scanning, and/or sequence analysis.

(See, e.g., Darras (2006) Continuum. 12: 33-75.) DNA extracted from blood or white cells can be used for such diagnoses. Deletions in the dystrophin gene are detected in 65% of patients with Duchenne muscular dystrophy and 85% of patients with Becker muscular dystrophy. Quantitative assays of dystrophin may be used to predict phenotype. Patients with Duchenne muscular dystrophy, for example, have less than 5% of the normal quantity of dystrophin. Patients with Becker muscular dystrophy have at least 20% normal dystrophin levels. (See Cardamone et al. (2008) Semin Neurol. 28:250-9.) Treatment of subjects having muscular dystrophy as shown by genetic testing is specifically contemplated.

Several forms of muscular dystrophy have been identified in the art. The methods and agents of the present invention may be used to treat any form of muscular dystrophy. In certain embodiments, the subject has a muscular dystrophy selected from the group consisting of Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

The present invention relates to methods and agents useful for treating muscular dystrophy in a subject. The subject can be, e.g., a skeletal muscle or an organism. The invention is applicable to a variety of different organisms, including, for example, vertebrates, large animals, and primates. In certain embodiments, the subject is a mammalian subject, and in particular embodiments, the subject is a human subject. Although applications with humans are clearly foreseen, veterinary applications are also envisaged herein.

In certain embodiments, the present methods of treatment involve administration of a therapeutically effective amount of an agent to a subject, wherein the agent inhibits CTGF, and wherein the subject would benefit from treatment of muscular dystrophy. In one aspect, the subject has muscular dystrophy. In another aspect, the subject has one or more clinical symptoms of muscular dystrophy.

Agents

In any of the methods described above, it is particularly contemplated that the agent or medicament that inhibits CTGF (i.e., the anti-CTGF agent or medicament) may be a polypeptide, polynucleotide, or small molecule; for example, an antibody that binds to CTGF, a CTGF antisense molecule, miRNA, ribozyme or siRNA, a small molecule chemical compound, etc. In particular, the present invention contemplates that inhibiting CTGF can be accomplished by any of the means well-known in the art for modulating the expression or activity of CTGF. Use of an agent or medicament that inhibits CTGF, for example, a human monoclonal antibody directed against CTGF, is preferred, although any method of inhibiting expression of the gene encoding CTGF, inhibiting production of CTGF, or inhibiting activity of CTGF is contemplated by the present invention.

Exemplary antibodies for use in the methods of the present invention are described, e.g., in U.S. Pat. No. 5,408,040; International Publication No. WO 99/07407; International Publication No. WO 99/33878; and International Publication No. WO 00/35936. Preferably, the anti-CTGF antibody for use in the method is a monoclonal antibody. Preferably the antibody is a neutralizing antibody. The antibody produced by ATCC Accession No. PTA-6006 cell line is such a preferred antibody. Exemplary monoclonal anti-CTGF antibodies for use in the methods of the present invention include CLN1 or mAb1 described in U.S. Pat. No. 7,405,274, which reference is incorporated by reference herein in its entirety. Variants of CLN1 that retain the binding and neutralization functions characteristic of CLN1 are also useful in the present invention. Such variants typically retain the variable regions of the heavy and/or light chain of the original neutralizing antibody, or minimally the complementarity determining regions (CDR) of heavy and light chains, and may contain substitutions and/or deletions in the amino acid sequences outside of those variable regions. Fragments and engineered versions of the original neutralizing antibody, e.g., Fab, F(ab)2, Fv, scFV, diabodies, triabodies, minibodies, chimeric antibodies, humanized antibodies, etc. are likewise useful in the method of the present invention. Such antibodies, or fragments thereof, can be administered by various means known to those skilled in the art. For example, antibodies are often injected intravenously, intraperitoneally, or subcutaneously.

Small molecule inhibitors of CTGF expression and/or activity have also been described; for example, International Publication No. WO 96/38172 identifies modulators of cAMP such as cholera toxin and 8Br-cAMP as inhibitors of CTGF expression. Therefore, compounds identified as, e.g., prostaglandin and/or prostacyclin analogs such as Iloprost (see, e.g., International Publication No. WO 00/02450; Ricupero et al. (1999) Am J Physiol 277:L1165-1171; also, see Ertl et al. (1992) Am Rev Respir Dis 145:A19), and potentially phosphodiesterase IV inhibitors (see, e.g., Kohyama et al. (2002) Am J Respir Cell Mol Biol 26:694-701), may be used to modulate CTGF expression. Also, inhibitors of serine/threonine mitogen activated protein kinases, particularly p38, cyclin-dependent kinase, e.g. CDK2, and glycogen synthase kinase (GSK)-3 have also been implicated in decreased CTGF expression. (See, e.g., Matsuoka et al. (2002) Am J Physiol Lung Cell Mol Physiol 283:L103-L112; Yosimichi et al. (2001) Eur J Biochem 268:6058-6065; International Publication No. WO 01/38532; and International Publication No. WO 03/092584.) Such compounds can be formulated and administered according to established procedures within the art.

Further, polynucleotide inhibitors of CTGF, including small interfering ribonucleic acids (siRNAs), micro-RNAs (miRNAs), ribozymes, and antisense sequences may be used in the present methods to inhibit expression and/or production of CTGF. (See, e.g., Kondo et al. (2000) Biochem Biophys Res Commun 278:119-124.) Such techniques are well-known to those of skill in the relevant art. Polynucleotide inhibitors that target CTGF expression have been described and utilized to reduce CTGF expression in various cell types. (See, e.g., International Publication No. WO 96/38172; International Publication No. WO 00/27868; International Publication No. WO 00/35936; International Publication No. WO 03/053340; Kothapalli et al. (1997) Cell Growth Differ 8(1): 61-68; Shimo et al. (1998) J Biochem (Tokyo) 124(1):130-140; Uchio et al. (2004) Wound Repair Regen 12:60-66; Guha et al. FASEB J. 2007 21:3355; U.S. Pat. Nos. 6,358, 741; 6,965,025; 7,462,602; US Application Publication No. 2008/0070856; US Application Publication No. 2008/0176964) CTGF antisense constructs and other types of polynucleotide inhibitors of CTGF can be used to reduce expression of CTGF and thereby treat muscular dystrophy or improve a clinical symptom of muscular dystrophy. Such constructs can be designed using appropriate vectors and expressional regulators for cell- or tissue-specific expression and constitutive or inducible expression. Such genetic constructs can be formulated and administered according to established procedures within the art.

Accordingly, in certain embodiments of the present invention, the agent or medicament that inhibits CTGF is an anti-CTGF antibody. In a preferred embodiment, the anti-CTGF antibody is a monoclonal antibody. In a particularly preferred embodiment, the antibody is a neutralizing antibody. In another preferred embodiment, the antibody is a human or humanized antibody to CTGF. In a more preferred embodiment, the antibody recognizes an epitope within domain 2 of CTGF. In a particular embodiment, the antibody is CLN1, as described in U.S. Pat. No. 7,405,274. In a particular embodiment, the antibody is the antibody produced by ATCC Accession No. PTA-6006 cell line, as described in U.S. Pat. No. 7,405,274. In another embodiment, the agent or medicament is a small molecule. In another embodiment, the agent or medicament is a polynucleotide inhibitor of CTGF. In particular embodiments, polynucleotide inhibitor is a CTGF antisense oligonucleotide, a CTGF miRNA, a CTGF ribozyme, or CTGF siRNA.

As further described herein, the agent or medicament that inhibits CTGF can be administered alone or in combination with other therapeutics, particularly therapeutics for treatment of muscular dystrophy or for improvement of a clinical symptom of muscular dystrophy. The present invention contemplates the use of the present methods in combination with other therapies. In one embodiment, the method is used in combination with another therapy, e.g., to further augment therapeutic effect on certain pathological events, etc. The two treatments may be administered at the same time or consecutively, e.g., during a treatment time course or following transplantation and rejection (acute or chronic). Current therapeutic approaches for the treatment of muscular dystrophy include the use of steroids (e.g., glucocorticoids, corticosteroiods), such as, for example, prednisone or deflazacort. In certain embodiments, the agent that inhibits CTGF is used in combination with an angiotensin converting enzyme inhibitor (ACEi), an angiotensin receptor blocker (ARB), a statin, a calcium channel blocker, a beta-blocker, a glucocorticoid, a corticosteroid, an advanced glycation endproduct (AGE) inhibitor, or a diuretic.

Use of any of these therapeutic agents in combination with the agents that inhibit CTGF (i.e., the anti-CTGF agents) for use in methods of the present invention is specifically contemplated, including use of an agent that inhibits CTGF for the preparation of a medicament for treating muscular dystrophy in a subject having muscular dystrophy, use of an agent that inhibits CTGF for the preparation of a medicament for improving a clinical symptom of muscular dystrophy in a subject having muscular dystrophy, use of an agent that inhibits CTGF for the preparation of a medicament for treating or preventing muscle (e.g., skeletal muscle) fibrosis in a subject having muscular dystrophy, use of an agent that inhibits CTGF for the preparation of a medicament for reducing muscle (e.g., skeletal muscle) degeneration or damage in a subject having muscular dystrophy, and use of an agent that inhibits CTGF for the preparation of a medicament for improving muscle (e.g., skeletal muscle) function or strength in a subject having muscular dystrophy.

For anti-CTGF antibody agents, depending on the type and severity of the disease, about 0.015 to 15 mg of antibody/kg of patient weight is an initial candidate dosage for administration to the patient, whether, for example, by one or more separate administrations, or by continuous infusion. Typically, a dose of between 0.5 and 10 mg/kg is used; preferably, a dose of between 1 mg/kg and 5 mg/kg is used. For repeated administrations over several days or longer, depending on the condition, the treatment is repeated until a desired suppression of disease symptoms occurs. However, other dosage regimens may be useful and are not excluded from the present invention.

Pharmaceutical Formulations and Routes of Administration

The anti-CTGF agents of the present invention can be delivered directly or in pharmaceutical compositions containing excipients, as is well known in the art. Present methods of treatment can comprise administration of an effective amount of an agent of the present invention to a subject having muscular dystrophy. In a preferred embodiment, the subject is a mammalian subject, and in a most preferred embodiment, the subject is a human subject.

An effective amount, e.g., dose, of agent or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the agent, dictate the type of formulation and the route of administration to be used, as well as whether local or systemic delivery would be preferred. In the methods of the present invention, preferred routes of administration include intraperitoneal, intravenous, and subcutaneous.

Pharmaceutical dosage forms of an agent of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the agent, such as, for example, syringes and needles, inhalers, pumps, injection pens, applicators, or special flasks. Pharmaceutical dosage forms are often composed of the agent, an excipient(s), and a container/closure system. One or multiple excipients, also referred to as inactive ingredients, can be added to an agent of the invention to improve or facilitate manufacturing, stability, administration, and safety of the agent, and can provide a means to achieve a desired drug release profile. Therefore, the type of excipient(s) to be added to the agent can depend on various factors, such as, for example, the physical and chemical properties of the agent, the route of administration, and the manufacturing procedure. Pharmaceutically acceptable excipients are available in the art, and include those listed in various pharmacopoeias. (See, e.g., USP, JP, EP, and BP, FDA web page, Inactive Ingredient Guide 1996, and Handbook of Pharmaceutical Additives, ed. Ash; Synapse Information Resources, Inc. 2002.)

Pharmaceutical dosage forms of an agent of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the agents of the present invention can include one or more physiologically acceptable inactive ingredients that facilitate processing of active molecules into preparations for pharmaceutical use.

Proper formulation is dependent upon the desired route of administration. For intravenous injection, for example, the agent may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the agents can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The agents may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the agent powder, suspension, or solution thereof can be delivered in a compatible hard or soft shell capsule.

In one embodiment, the agents of the present invention can be administered topically, such as through a skin patch, a semi-solid or a liquid formulation, for example a gel, a (micro-) emulsion, an ointment, a solution, a (nano/micro)-suspension, or a foam. The penetration of the agent into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of an agent of the invention. Transdermal or topical administration would be preferred, for example, in situations in which local delivery with minimal systemic exposure is desired.

For administration by inhalation, or administration to the nose, the agents for use according to the present invention are conveniently delivered in the form of a solution, suspension, emulsion, or semisolid aerosol from pressurized packs, or a nebuliser, usually with the use of a propellant, e.g., halogenated carbons dervided from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the agent and a suitable powder base such as lactose or starch.

Agents formulated for parenteral administration by injection are usually sterile and, can be presented in unit dosage forms, e.g., in ampoules, syringes, injection pens, or in multi-dose containers, the latter usually containing a preservative. The agents may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of an agent of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the agents of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving agents of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

The therapeutically effective amount is the amount of the agent or pharmaceutical composition that will elicit the biological or medical response of a cell, tissue, organ, system, animal, or human that is being sought by the researcher, veterinarian, medical doctor, or other clinician, e.g., an improvement in one or more clinical symptoms of muscular dystrophy. For agents useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population).

The dose ratio of toxic to therapeutic effects is the therapeutic index, which can be expressed as the ratio LD50/ED50. Agents that exhibit high therapeutic indices are preferred.

The effective amount or therapeutically effective amount is the amount of the agent or pharmaceutical composition that will elicit the biological or medical response of a tissue, system, animal, or human that is being sought by the researcher, veterinarian, medical doctor, or other clinician, e.g., reduced muscle damage, reduced fibrosis, etc.

Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, e.g., improved muscle function, decreased muscle damage, etc, i.e., minimal effective concentration (MEC). The MEC will vary for each agent but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present agents and compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising an agent of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1

Reduced CTGF Levels Ameliorates Fibrosis in Dystophic Skeletal Muscle in an Animal Model of Duchenne Muscular Dystrophy The mdx mouse is an animal model of Duchenne muscular dystrophy. In the mdx mouse, the dystrophin protein is absent in skeletal muscle and many similar pathological features seen in muscle in human subject with Duchenne muscular dystrophy are observed in these animals. (See e.g., Bulfield et al. (1984) PNAS 81:1189-1192; Stedman et al. (1991) Nature 352:536-539. ) In this animal model of Duchenne muscular dystrophy, skeletal muscle fibrosis can be assessed by measuring skeletal muscle levels of extracellular matrix proteins (e.g., fibronectin, periostin). (See e.g., Mezzano et al. (2007) J Cell Commun Signal. 1:205-17. ) The effects of reduced CTGF levels on fibrosis in dystrophic skeletal muscle were examined using the mdx mouse model of Duchenne muscular dystrophy as follows.

In this series of experiments, in order to reduce CTGF levels, mdx mice were mated with $CTGF^{(+/-)}$ mice, in which exon 1 of one CTGF allele is replaced by a neomycin resistance gene, resulting in lowered CTGF expression. (See, e.g., Ivkovic et al. (2003) Development 130:2779-2791. ) Offspring male mdx-$CTGF^{(+/-)}$, mdx, and C57BL control mice were used in the following study. At three months of age, mdx-$CTGF^{(+/-)}$, mdx, and control mice were sacrificed and their skeletal muscles (tibialis anterior and diaphragm) removed for analysis of extracellular matrix protein levels.

Fibronectin and periostin, two extracellular matrix proteins, were selected as markers of muscle fibrosis and impaired muscle regeneration. Muscle samples from the tibialis anterior and diaphragm were analyzed for the expression levels of fibronectin and periostin by standard immunoblot techniques. Briefly, cell extracts obtained from the skeletal muscle samples were prepared in 1% SDS buffer (50 mM Tris-HCl, pH 7.4, 0.15 M NaCl, 1% sodium dodecyl sulfate and 1 mM PMSF). Cell extract aliquots were subjected to SDS gel electrophoresis in 8% or 10% polyacrylamide gels, electrophoretically transferred onto polyvinylidene fluoride membranes (Immobilon-P), and probed with rabbit anti-fibronectin (1:10,000; Sigma-Aldrich, USA) or rabbit anti-periostin antibodies. Anti-rabbit horseradish peroxidase (Pierce, USA) was used for detection and all immunoreactions were visualized by enhanced chemiluminescence (Pierce, USA).

Figure 1B:
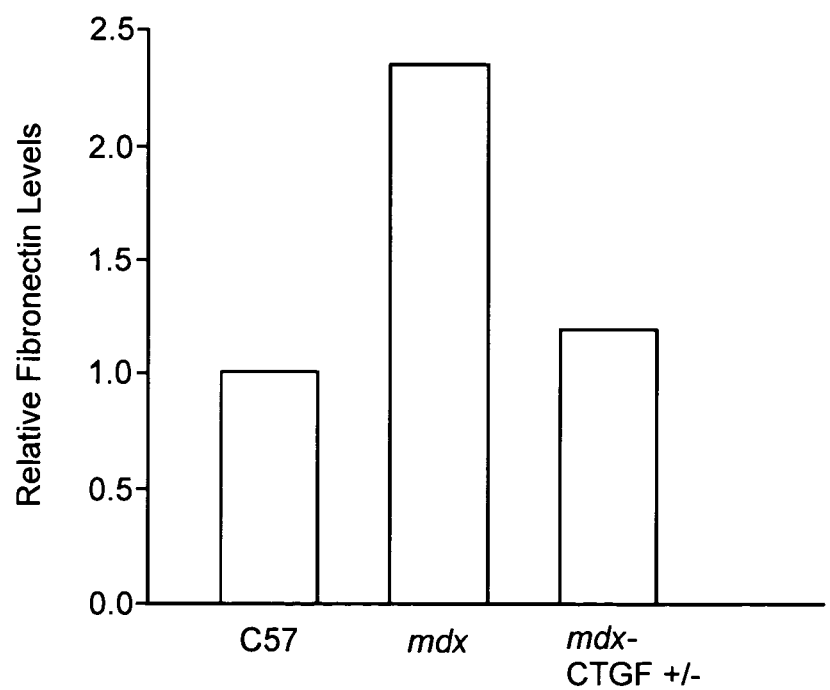
Figure 2A:
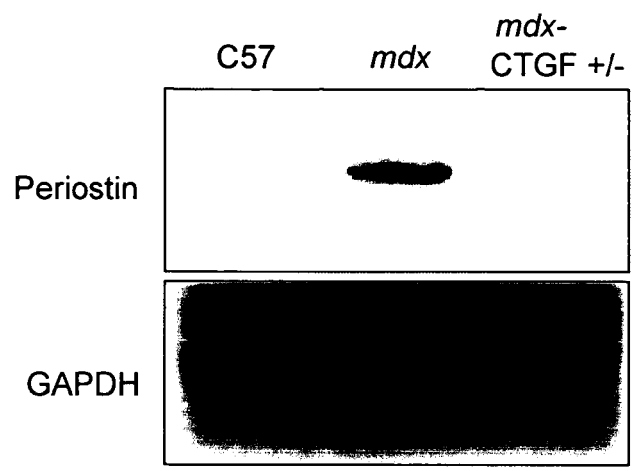
FIGS. 2A and 2B set forth data showing methods and agents of the present invention reduced periostin levels in dystrophic skeletal muscle in an animal model of muscular dystrophy.
Figure 2B:
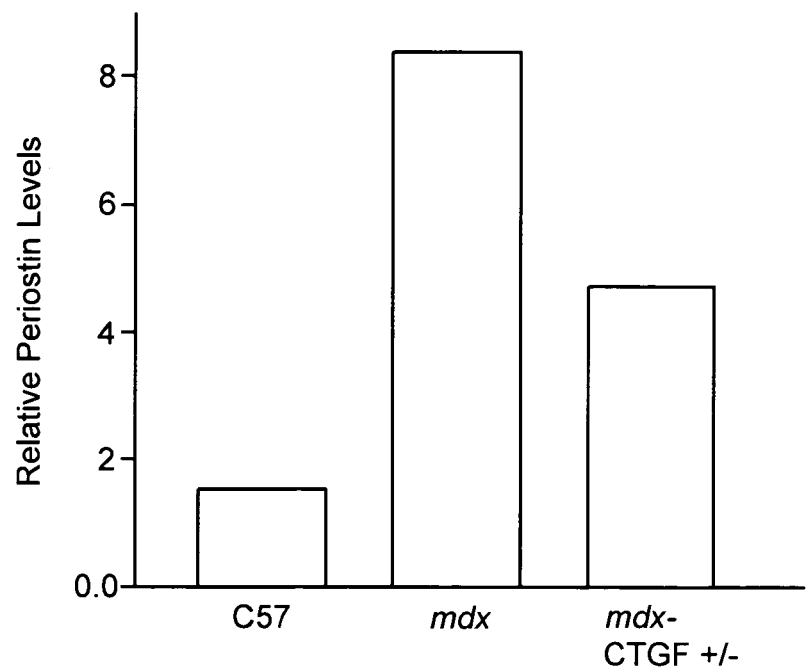

CTGF levels were reduced in the mdx-$CTGF^{(+/-)}$ as compared to the levels of CTGF observed in mdx mice. (Data not shown.) As shown in FIGS. 1A and 1B, fibronectin levels were increased in the muscle of mdx mice compared to the levels observed in the muscle of control mice. Similarly, as shown in FIGS. 2A and 2B, periostin levels were increased in the muscle of mdx mice compared to those observed in the muscle of control mice. The mdx-$CTGF^{(+/-)}$ mice, however, which had reduced CTGF expression compared to mdx mice, had lower muscle fibronectin and periostin levels compared to those observed in mdx mice. (See FIGS. 1A, 1B, 2A, and 2B.)

These results showed that reduced CTGF expression resulted in reduced fibronectin and periostin protein levels in muscle in an animal model of Duchenne muscular dystrophy. The extent of muscle fibrosis can be assessed by extracellular matrix protein levels; therefore, these results showed that methods of the present invention are effective at reducing muscle fibrosis in Duchenne muscular dystrophy in a subject by reducing CTGF levels. Further, these results indicated that methods and agents of the present invention would be effective at treating muscular dystrophy.

In another series of experiments, mice were subjected to exercise on a treadmill to accelerate skeletal muscle fibrosis (i.e., exercise-injured skeletal muscle). Exercise of the mdx mouse accelerates muscle damage in this model (i.e. worsen the dystrophic condition). (See, e.g., De Luca et al. (2005) Am J Pathol. 166:477-89. ) Male C57BL/6J, mdx, and mdx- CTGF$^{(+/-)}$ mice aged 4 weeks were randomized into sedentary and exercise groups. Mice in the exercise group were exercised on a treadmill (Columbus Instruments, USA) for 30 minutes, twice a week, at a rate of 12 m/min during the second and fourth month of the study. All mice were sacrificed at 5 months of age and their skeletal muscles (tibialis anterior and diaphragm) were removed for immunoblot analysis of fibronectin levels as described above. Additionally, muscle sections were analyzed by immunohistochemistry for fibronectin expression using standard techniques known in the art.

Figure 3A:
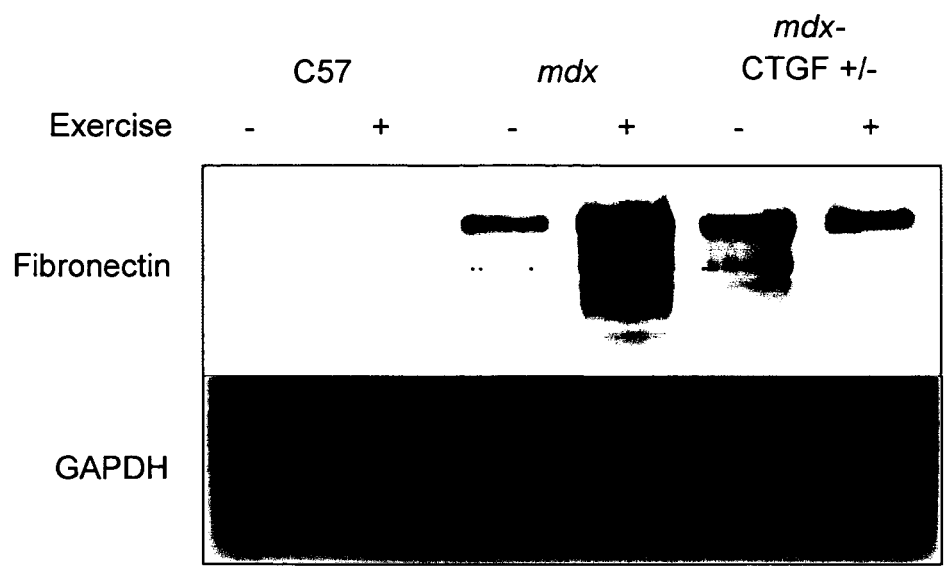
FIGS. 3A and 3B set forth data showing methods and agents of the present invention reduced fibronectin levels in exercised dystrophic skeletal muscle in an animal model of muscular dystrophy.
Figure 3B:
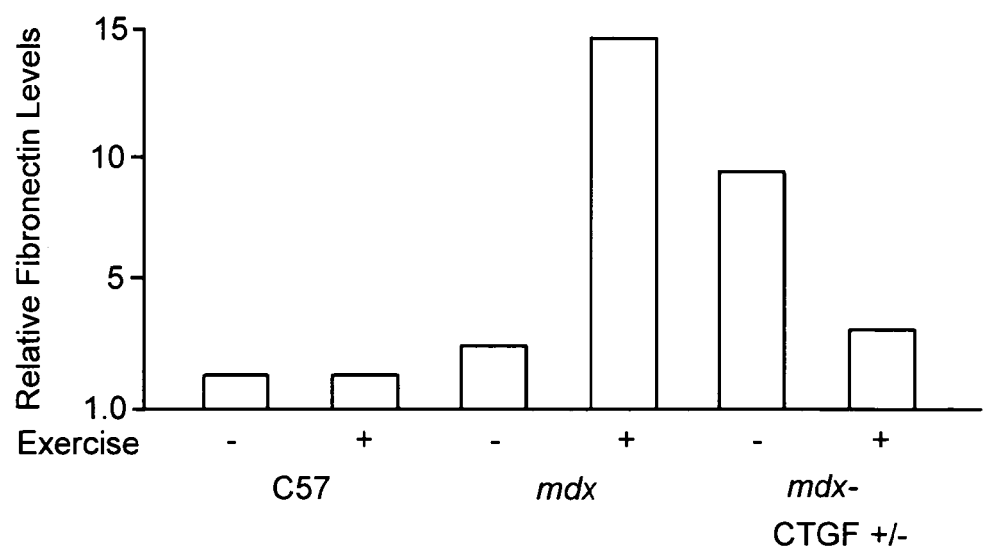
Figure 4:
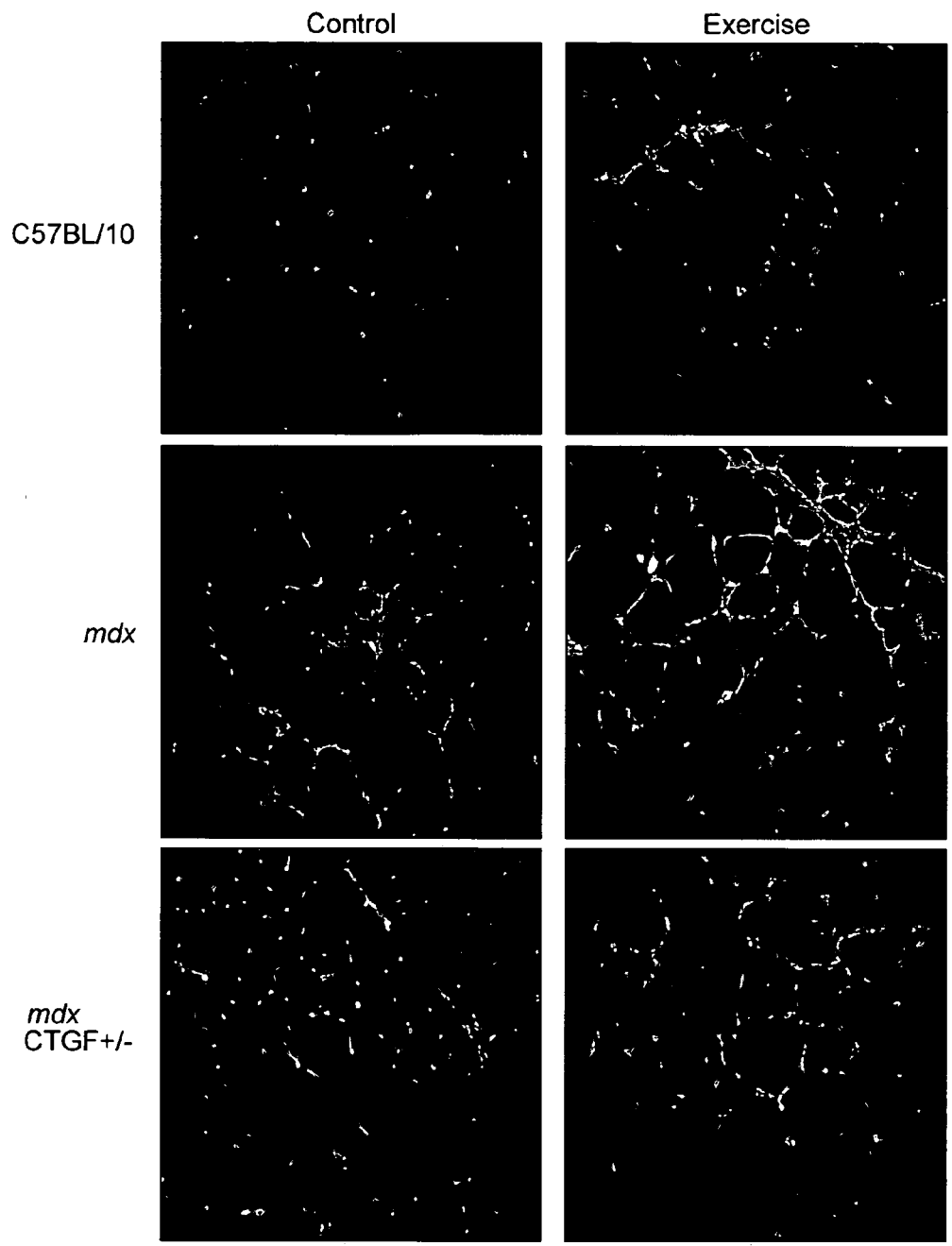
FIG. 4 sets forth data showing methods and agents of the present invention reduced fibronectin levels in exercised dystrophic skeletal muscle in an animal model of muscular dystrophy.

As shown in FIGS. 3A and 3B (immunoblot), and FIG. 4 (immunohistochemistry), levels of fibronectin were increased in the muscle of exercised mdx mice compared to those observed in the muscle of exercised control mice. This data showed that exercise enhanced muscle fibronectin expression and indicated that exercise resulted in the induction of muscle fibrosis in mdx mice. The exercised mdx-CTGF$^{(+/-)}$ mice, however, which had reduced CTGF expression compared to mdx mice, had lower fibronectin levels compared to those observed in exercised mdx mice. This data showed that reduced CTGF expression in exercised mdx mice resulted in decreased fibronectin levels and, therefore, decreased skeletal muscle fibrosis.

These results showed that reduced CTGF expression resulted in lower fibronectin levels in skeletal muscle in an animal model of Duchenne muscular dystrophy. As the extent of skeletal muscle fibrosis can be assessed by extracellular matrix protein levels (e.g., fibronectin), these results showed that methods and agents of the present invention are effective at reducing muscle fibrosis in Duchenne muscular dystrophy in a subject by reducing or inhibiting CTGF. Further, these results suggested that agents and methods of the present invention would be effective for treating muscular dystrophy.

Example 2

CTGF Inhibition Ameliorates Dedifferentiation of Skeletal Muscle Cells in Vitro

Myoblasts are muscle precursor cells that play an important role in the growth and repair of skeletal muscle following injury. Pathological dedifferentiation of myoblasts has been observed in muscular dystrophy and contributes to disease progression. (See Vial et al. (2008) J Cell Physiol. 215:410-21.) Myoblast dedifferentiation is characterized, in part, by down regulation of MyoD, myogenin, myosin, and desmin, markers of myoblast activation and differentiation. Therefore, the effect of CTGF inhibition on myoblast dedifferentiation is examined as follows.

In a series of experiments, C2C12 myoblasts (ATTC, Manassas, Va.) are transfected with a specific siRNA for CTGF or incubated with an anti-CTGF antibody (e.g., the anti-CTGF antibody CLN-1). The myoblasts are then cultured and induced to dedifferentiate in the presence of angiotensin II, as described in Larrain et al. ((1997) Exp Cell Res. 234:405-12). Following incubation with angiotensin II, myoblast activation and dedifferentiation is assessed by measuring the expression levels of myoblast specific proteins (e.g., myogenin, myosin, myoD, and desmin) by real time PCR, Northern blot or western blot analysis. (See Caceres et al. (2000) Eur J Cell Biol 79:173-81; Cohn et al. (2007) Nat Med. 13:204-10; Droppelmann et al. (2009) J Biol Chem epub.)

Transfection of myoblasts with siRNA for CTGF or treatment of myoblasts with an anti-CTGF antibody decreases myoblast dedifferentiation as measured by a reduction in down regulation of MyoD and desmin levels as compared to non-treated cells. Similarly, transfection of myoblasts with siRNA for CTGF or treatment of myoblasts with an anti-CTGF antibody increases myoblast activation (as measured by increased expression levels of myogenin and myosin). These results indicate that inhibition of CTGF ameliorates angiotensin-induced dedifferentiation in skeletal muscle cells. As the extent of dedifferentiation of myoblasts is assessed by measurement of decreases in expression of myoblast markers, these results suggest that inhibition of CTGF reduces dedifferentiation of skeletal muscle cells in a subject with muscular dystrophy. These results further suggest that inhibition of CTGF, using the methods and agents of the present invention, would provide an effective treatment for muscular dystrophy.

Example 3

CTGF Inhibition Ameliorates Fibrosis in Skeletal Muscle Cells

Myogenic precursor cells can differentiate into myofibroblasts after muscle injury and myofibroblasts contribute to the development of fibrosis. Increased myofibroblast activation has been observed in skeletal muscle cells treated with angiotensin II. The effect of CTGF inhibition on angiotensin-induced myofibroblast activity is examined as follows.

C2C12 myofibroblasts (ATTC, Manassas, Va.) are transfected with a specific siRNA for CTGF or incubated with an anti-CTGF antibody (e.g., the anti-CTGF antibody CLN-1). Myofibroblasts are then incubated in the presence of angiotensin II as described in Larrain et al. ((1997) Exp Cell Res. 234:405-12). The expression levels in muscle of several extracellular matrix proteins (e.g., fibronectin, periostin, thrombospondin-1, decorin, and collagen III) are evaluated by real time PCR, Northern blot and/or western blot analysis. (See Caceres et al. (2000) Eur J Cell Biol 79:173-81; Cohn et al. (2007) Nat Med. 13:204-10; Droppelmann et al. (2009) J Biol Chem epub.) The extent of fibrosis is assessed by measuring increases in the expression levels of various extracellular matrix proteins in muscle.

Transfection of myoblasts with siRNA for CTGF or treatment of myoblasts with an anti-CTGF antibody (e.g., the anti-CTGF antibody CLN-1) decreases myofibroblast activation as shown by decreased levels of extracellular matrix proteins (e.g., decreased expression levels of fibronectin, periostin, thrombospondin-1, decorin, and collagen III). These results indicate that inhibition of CTGF decreases angiotensin-induced fibrosis in skeletal muscle cells (e.g., myofibroblasts) and suggest that inhibition of CTGF reduces fibrosis of skeletal muscle cells in a subject with muscular dystrophy. These results further suggest that inhibition of CTGF, using the methods and agents of the present invention, would provide an effective treatment for muscular dystrophy.

In one series of experiments, the effect of CTGF inhibition on CTGF-mediated myofibroblast activity was examined as follows.

C2C12 myofibroblasts (ATTC, Manassas, Va.) were infected with adenoviral CTGF and subsequently serum starved for 24 hours. Next, conditioned media with or without three different volumes of an anti-CTGF antibody (CLN-1, 40 ug/ml) was added to the starved myofibroblasts. Following incubation with conditioned media, protein levels of the extracellular matrix protein fibronectin were evaluated by western blot analysis. (See Caceres et al. (2000) Eur J Cell Biol 79:173-81; Cohn et al. (2007) Nat Med. 13:204-10; Droppelmann et al. (2009) J Biol Chem epub.) The extent of myofibroblast activity and CTGF-mediated fibrosis was assessed by measuring increases in the levels of the extracellular matrix protein fibronectin.

Figure 5:
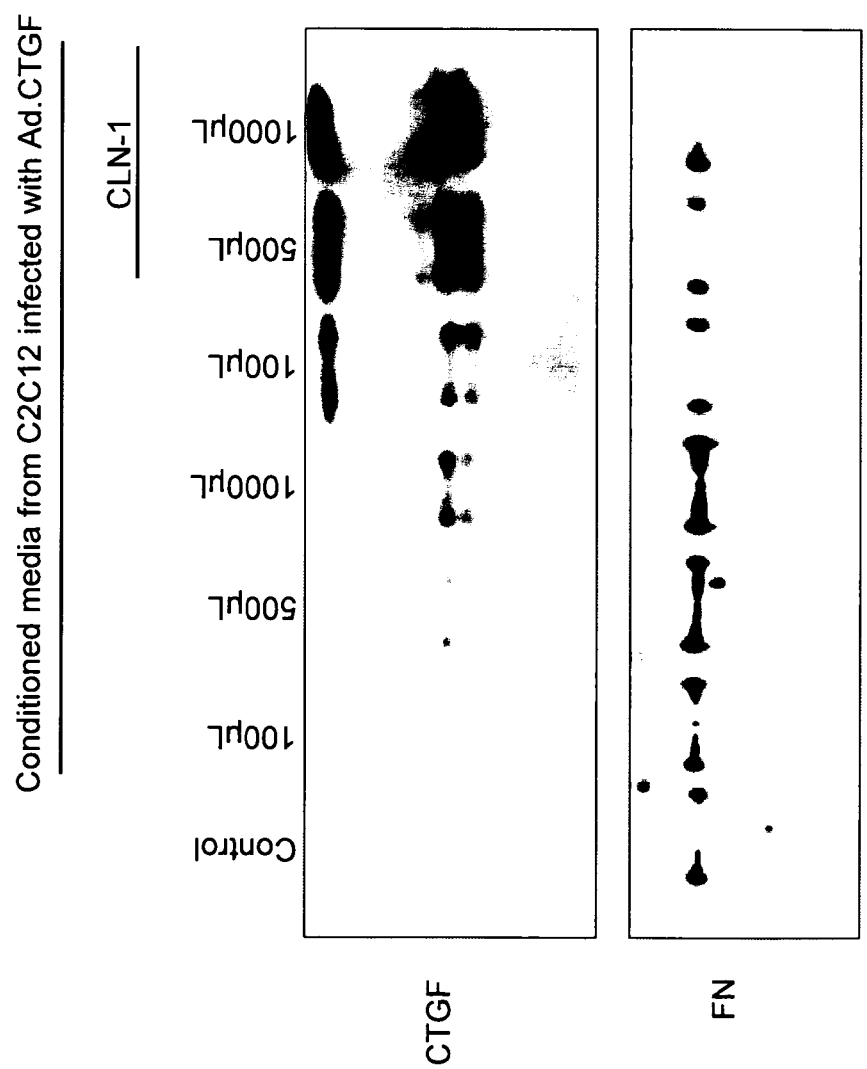
FIG. 5 sets forth data showing methods and agents of the present invention reduced CTGF-mediated myofibroblast activity.

As shown in FIG. 5, addition of conditioned media to myofibroblasts infected with adenoviral CTGF increased myofibroblast activation as shown by increased levels of the extracellular matrix protein fibronectin compared to levels in control myofibroblasts. In contrast, treatment of infected myofibroblasts with an anti-CTGF antibody (CLN-1) decreased myofibroblast activation as shown by decreased levels of fibronectin (see FIG. 5). These results indicated that inhibition of CTGF decreased CTGF-mediated fibrosis in skeletal muscle cells (e.g., myofibroblasts) and suggested that inhibition of CTGF would reduce fibrosis of skeletal muscle cells in a subject with muscular dystrophy. These results further suggested that inhibition of CTGF, using the methods and agents of the present invention, would provide an effective treatment for muscular dystrophy.

Example 4

CTGF Inhibition Reduces Damage to Dystrophic Skeletal Muscle in an Animal Model of Duchenne Muscular Dystrophy The mdx mouse is an animal model of Duchenne muscular dystrophy. The effect of methods and agents of the present invention on muscle function is examined using the mdx mouse model of Duchenne muscular dystrophy as follows.

Four-week old male mdx and control (C57BL/10J) mice are randomly assigned to a sedentary group or an exercise group. Exercise of the mdx mouse has been shown to accelerate muscle damage in this model (i.e. worsen the dystrophic condition). (See, e.g., De Luca et al. (2005) Am J Pathol. 166:477-89.) Mice are randomized into two treatment groups and treated as follows. Group 1 is treated with anti-CTGF antibody (CLN-1, 10 mg/kg; see International Publication No. WO 2004/108764) and Group 2 is treated with an isotype-matched control human IgG (IgG, 10 mg/kg)). Antibodies are administered i.p. at doses of 10 mg/kg (approximate injection volume of 0.5 ml) three times weekly for up to eight weeks.

The control and mdx mice in the exercised groups are subjected to 30 minutes of running on a horizontal treadmill (Columbus Instruments, USA) at 12 meters/minute, twice a week, for up to 8 weeks. (See, e.g., Luca et al. (2005)). Body weight is monitored in all animals throughout the duration of the study to assess changes in muscle mass. Blood samples are collected at various timepoints and serum creatine kinase (a marker of muscle damage) levels are determined for each sample using a commercial assay (Valtek, Santiago, Chile; See, e.g., Osses and Brandan (2002) Am J Physiol Cell Physiol. 282:C383-94). An increase in serum creatine kinase levels indicates an increase in muscle damage.

After the last treatment, animals are sacrificed and their tibialis anterior and diaphragm muscles removed to assess the presence and extent of muscle damage and fibrosis. Muscle fibrosis is determined by measuring the extracellular matrix protein content of the muscle samples. A portion of each muscle sample is homogenized for protein analysis and another portion is snap frozen for subsequent immunohistochemical analysis. Homogenized muscle samples are incubated with the following extracellular matrix protein antibodies: fibronectin; periostin; thrombospondin-1; decorin; and collagen III. Following incubation, samples are subsequently separated by SDS-PAGE using standard techniques. (See, e.g., Casar et al. (2004) Dev Biol. 268:358-71; Droppelmann et al. (2009) J Biol Chem; Fadic et al. (2006) J Cell Mol Med. 10:758-69.) For immunohistochemical analysis, frozen muscle samples are sectioned on a cryostat and the resulting sections treated with specific antibodies for the ECM proteins described above.

Skeletal muscles from exercised animals administered a control IgG antibody show increased extracellular matrix protein levels, indicating an increase in muscle fibrosis. Muscle fibrosis in exercised animals administered an agent that inhibits CTGF, however, is reduced as shown by a reduction in extracellular matrix protein levels.

Additionally, exercised animals administered an agent that inhibits CTGF show reduced serum creatine kinase levels as compared to serum creatine kinase levels observed in animals administered control IgG antibody, indicating that muscle damage is reduced by inhibition of CTGF. Muscle damage and muscle fibrosis are clinical symptoms of muscular dystrophy. Therefore, these results show that inhibition of CTGF reduces or treats clinical symptoms of muscular dystrophy. These results further suggest that inhibition of CTGF, using the methods and agents of the present invention, would provide an effective treatment for muscular dystrophy.

In one series of experiments, the effect of methods and agents of the present invention on muscle function was examined using the mdx mouse model of Duchenne muscular dystrophy as follows.

Four-month old male mdx and control (C57BL/10J) mice were used in these studies. All mice were exercised for eight weeks as described below. Mdx mice were randomized into two treatment groups and treated as follows. Group 1 was treated with anti-CTGF antibody (CLN-1, 10 mg/kg; see International Publication No. WO 2004/108764) and Group 2 was treated with an isotype-matched control human IgG (IgG, 10 mg/kg)). Antibodies were administered i.p. at doses of 10 mg/kg (approximate injection volume of 0.5 ml) three times weekly for eight weeks.

To exercise the animals, control and mdx mice were subjected to 30 minutes of running on a horizontal treadmill (Columbus Instruments, USA) at 12 meters/minute, twice a week, for eight weeks. (See, e.g., Luca et al. (2005)). Body weight was monitored in all animals throughout the duration of the study to assess changes in muscle mass and fibrosis. An increase in body weight in the mdx mice indicates an increase in muscle damage and fibrosis.

After the last treatment, an exercise resistance test was performed on all animals. Briefly, the animals were subjected to 5 minutes of running on a horizontal treadmill (Columbus Instruments, USA) at 15 meters/minute. The treadmill was marked at a point ⅓ of the way down from the front of the treadmill. In this test, animals stop running when they become fatigued. Each time an animal stopped running and passed the mark on the treadmill an "event" was counted. The total number of events observed during the 5 minutes of exercise was recorded. A greater number of events indicate an increase in muscle damage and a decrease in muscle strength.

Following the exercise resistance test, animals were sacrificed and their tibialis anterior and diaphragm muscles removed to assess the presence and extent of muscle damage and fibrosis. Muscle fibrosis was determined by measuring the extracellular matrix protein content of the muscle samples. A portion of each muscle sample was homogenized for protein analysis and another portion was snap frozen for subsequent immunohistochemical analysis. Homogenized muscle samples were incubated with extracellular matrix protein antibodies against fibronectin and collagen III. Following incubation, samples were subsequently separated by SDS-PAGE using standard techniques. (See, e.g., Casar et al. (2004) Dev Biol. 268:358-71; Droppelmann et al. (2009) J Biol Chem; Fadic et al. (2006) J Cell Mol Med. 10:758-69.) For immunohistochemical analysis, frozen muscle samples were sectioned on a cryostat and the resulting sections treated with specific antibodies for the extracellular matrix proteins described above.

Figure 6:
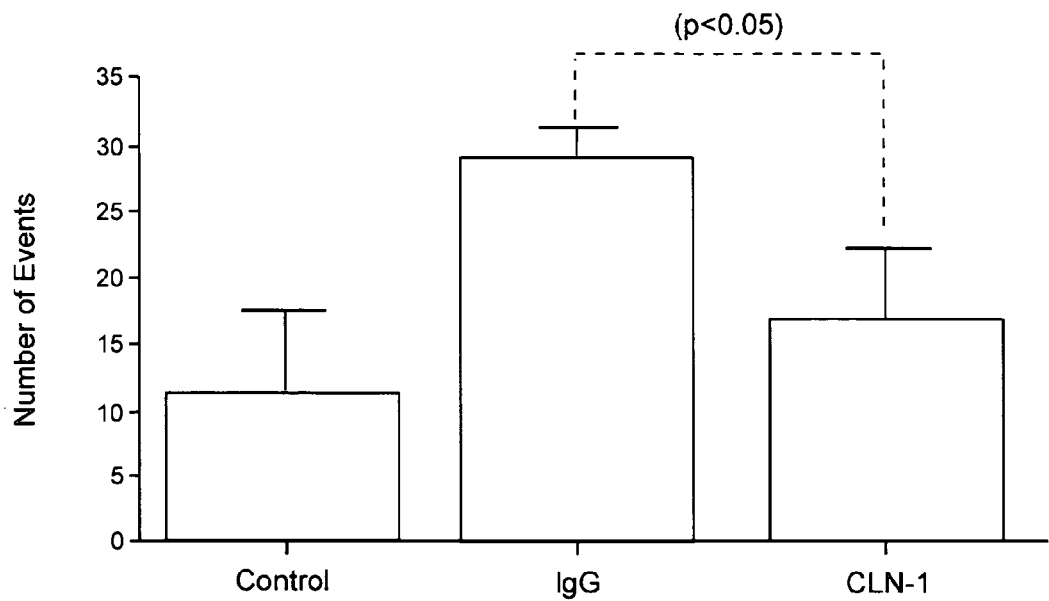
FIG. 6 sets forth data showing methods and agents of the present invention decreased the number of events during an exercise resistance test in an animal model of muscular dystrophy.

As shown in FIG. 6, compared to healthy control animals, exercised mdx animals administered a control IgG antibody showed an increased number of events during an exercise resistance test, indicating increased muscle damage and decreased muscle strength. In contrast, exercised mdx mice administered an agent that inhibits CTGF showed a significantly decreased number of events (i.e. less muscle damage and greater muscle strength) compared to that observed in exercised mdx mice administered control IgG antibody (see FIG. 6).

These results showed that methods and agents of the present invention were effective at reducing muscle damage and improving muscle strength in an animal model of muscular dystrophy. Muscle damage and reduced muscle strength are clinical symptoms of muscular dystrophy. Therefore, these results showed that inhibition of CTGF reduced or treated clinical symptoms of muscular dystrophy. These results further suggested that inhibition of CTGF, using the methods and agents of the present invention, provides an effective treatment for muscular dystrophy.

Figure 7A:
FIGS. 7A and 7B set forth data showing methods and agents of the present invention reduced fibronectin levels in exercised dystrophic skeletal muscle in an animal model of muscular dystrophy.
Figure 7B:
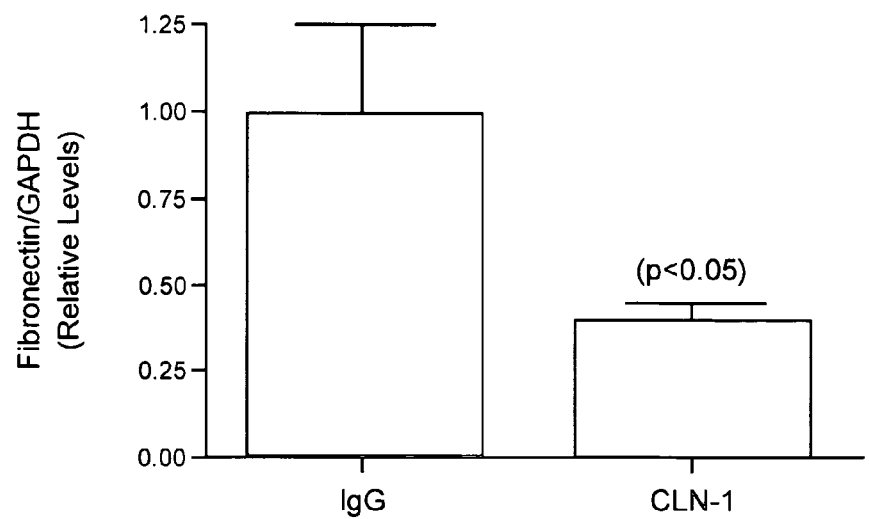
Figure 8A:
FIGS. 8A, 8B, 8C, and 8D set forth data showing methods and agents of the present invention reduced fibronectin levels in exercised dystrophic skeletal muscle in an animal model of muscular dystrophy.
Figure 8B:
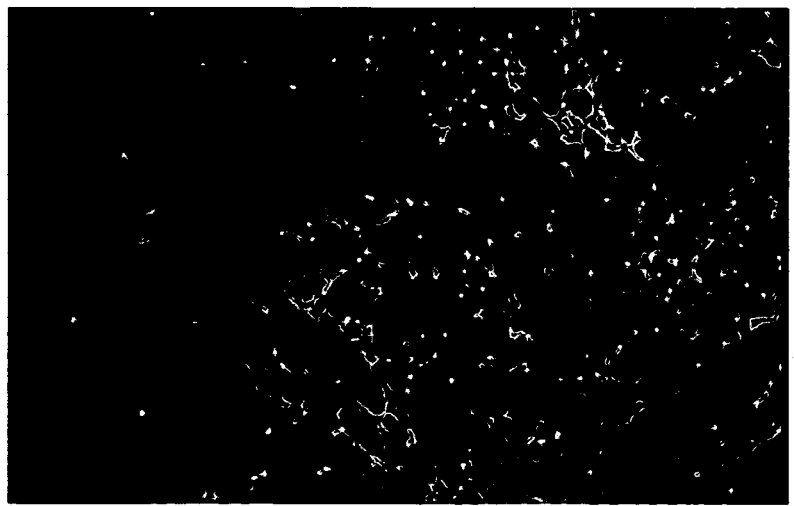
Figure 8C:
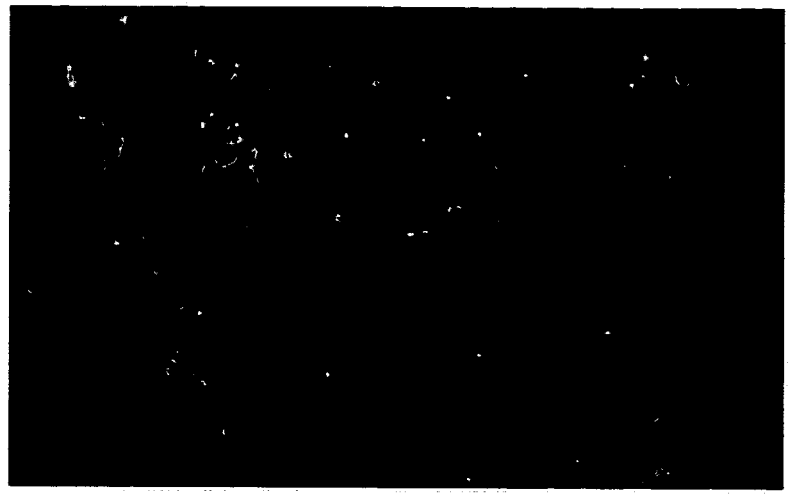
Figure 8D:

As shown in FIGS. 7A (immunoblot) and 7B, and FIGS. 8A and 8B (immunohistochemistry), skeletal muscles from exercised animals administered a control IgG antibody showed increased fibronectin levels. In contrast, exercised mdx mice administered an agent that inhibits CTGF showed reduced fibronectin levels as compared to that observed in animals administered a control IgG antibody (see FIGS. 7A and 7B, and FIGS. 8C and 8D).

Figure 9A:
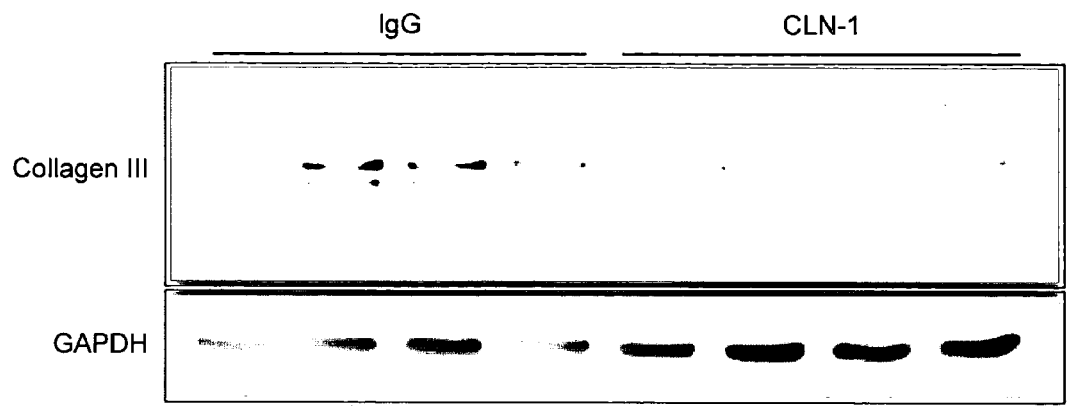
FIGS. 9A and 9B set forth data showing methods and agents of the present invention reduced collagen III levels in exercised dystrophic skeletal muscle in an animal model of muscular dystrophy.
Figure 9B:
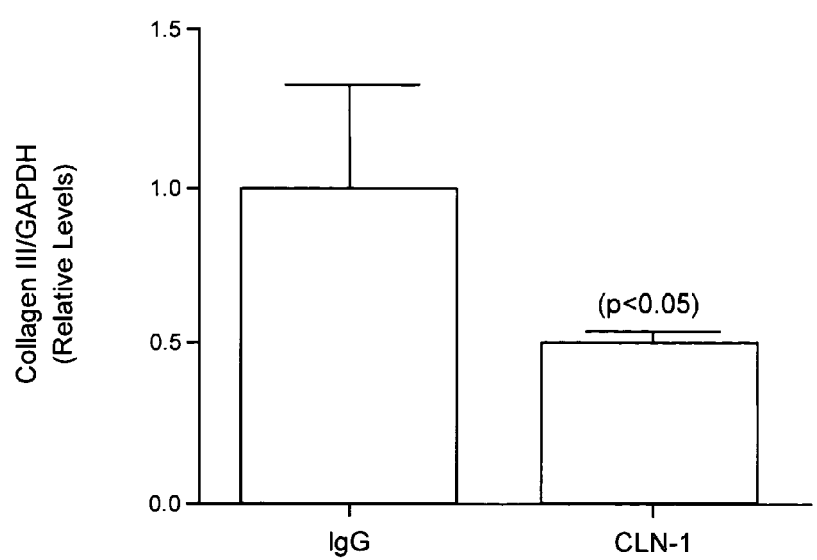
Figure 10A:
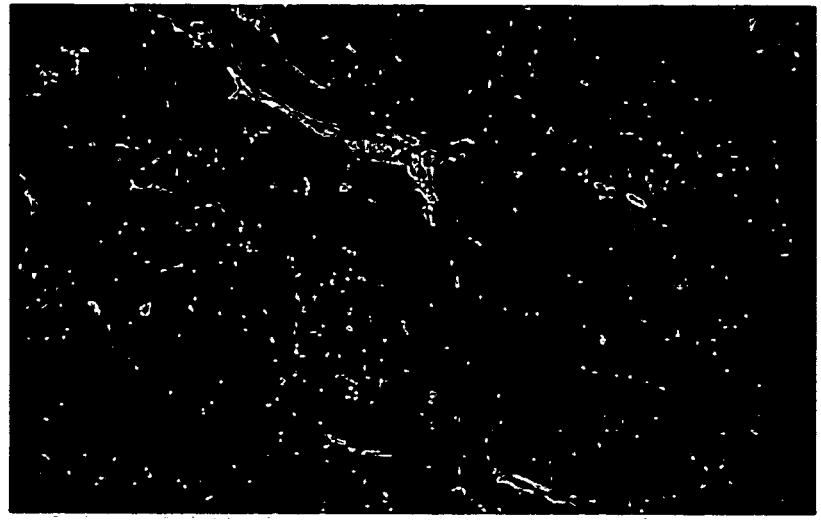
FIGS. 10A, 10B, 10C, and 10D set forth data showing methods and agents of the present invention reduced collagen III levels in exercised dystrophic skeletal muscle in an animal model of muscular dystrophy.
Figure 10B:
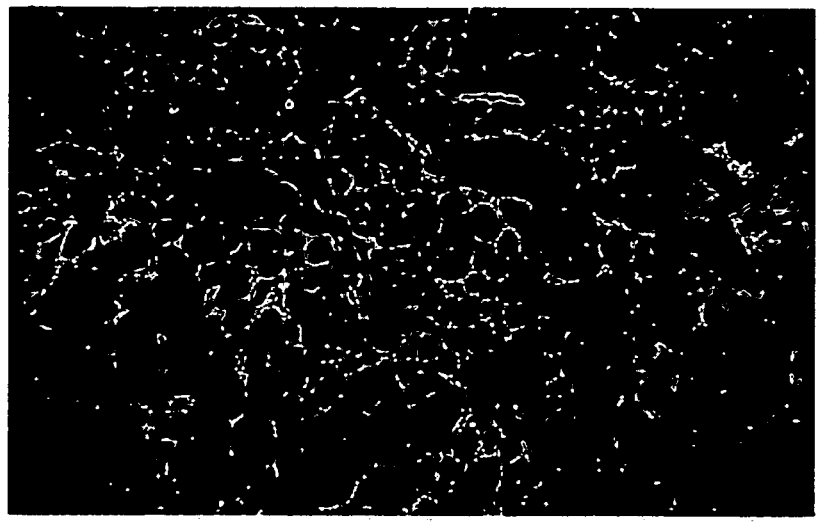
Figure 10C:
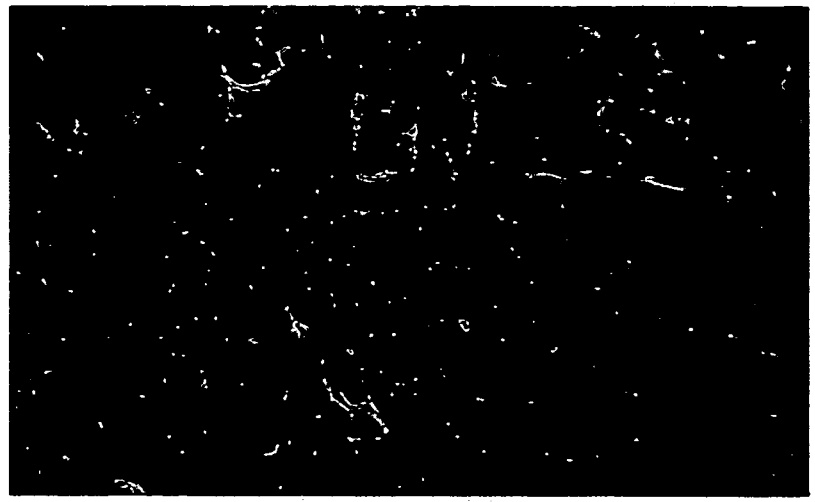
Figure 10D:
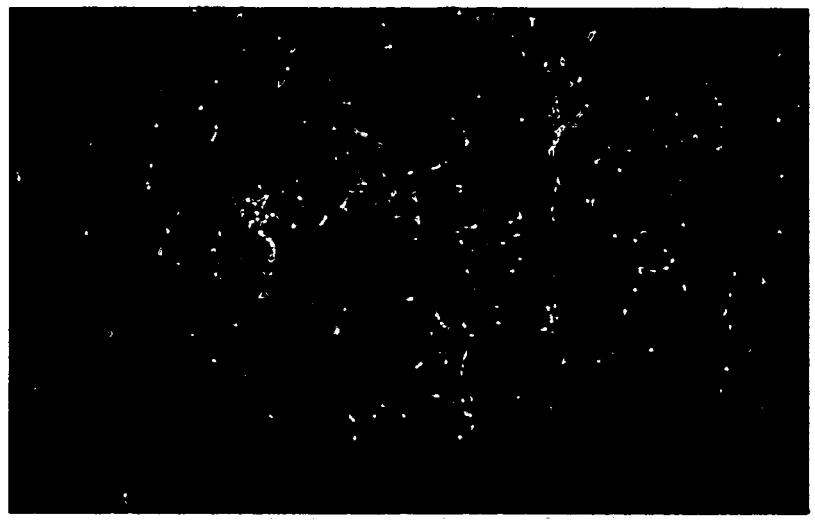
Figure 12A:
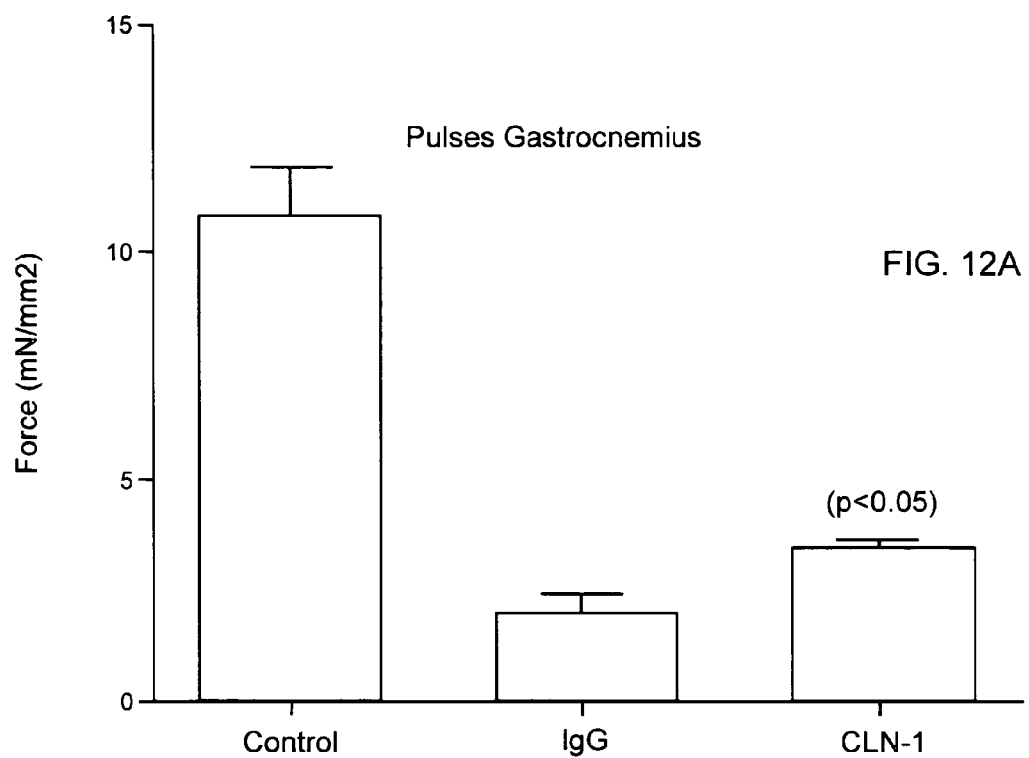
FIGS. 12A, 12B, 12C, and 12D set forth data showing methods and agents of the present invention improved muscle function in an animal model of muscular dystrophy.
Figure 12B:
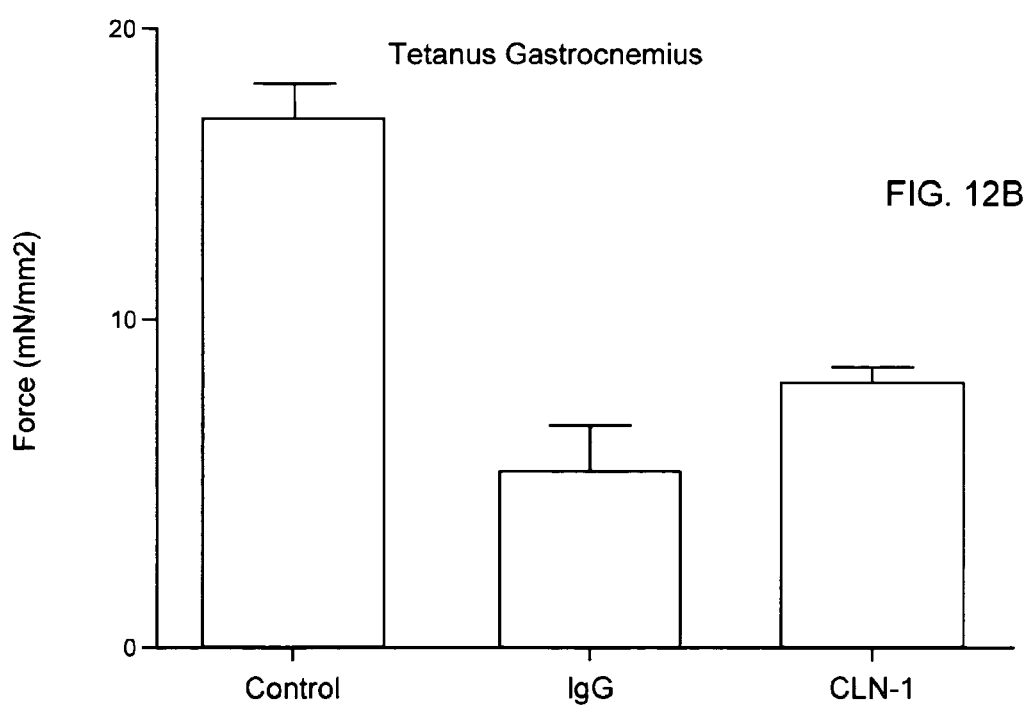
Figure 12C:
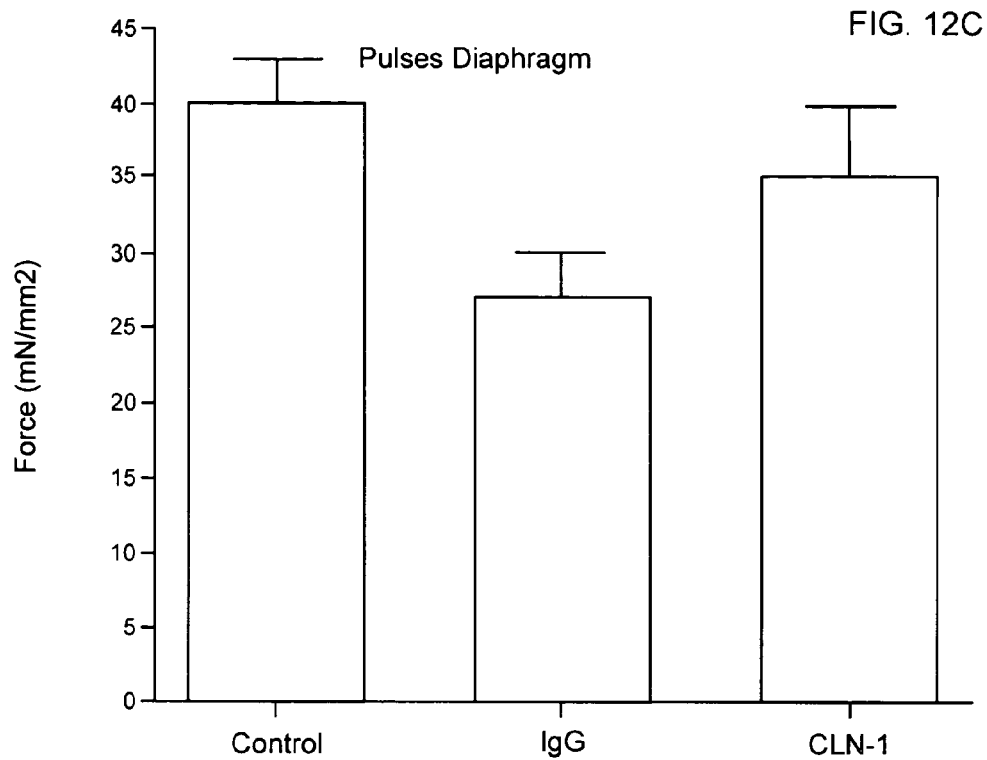
Figure 12D:
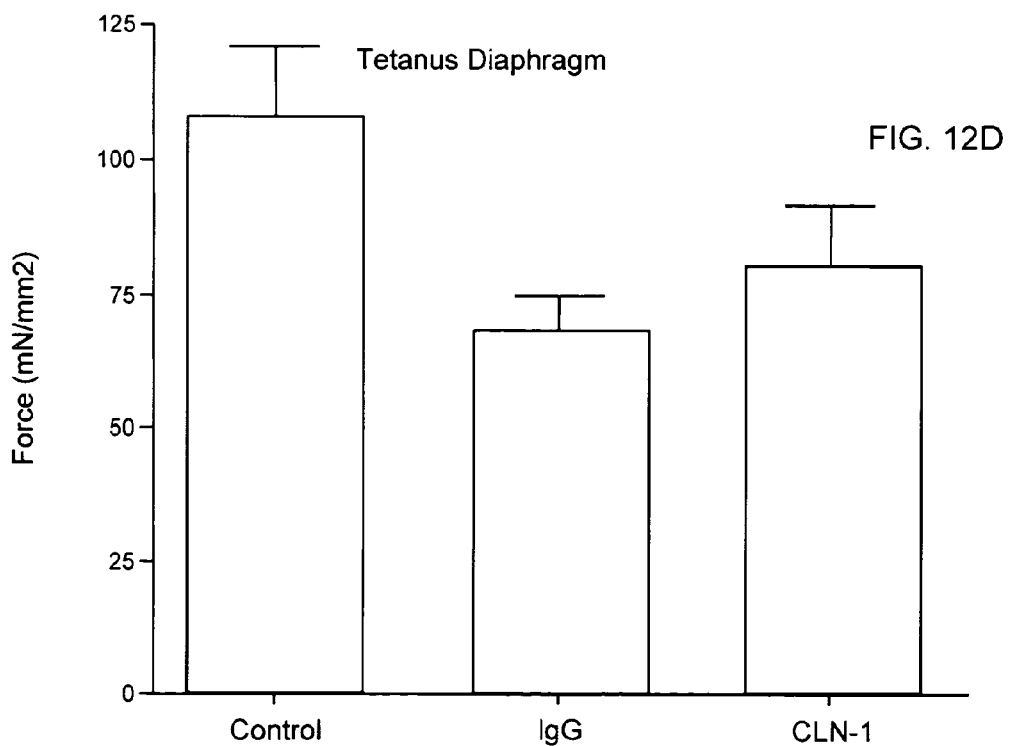

As shown in FIGS. 9A (immunoblot) and 9B, and FIGS. 10A and 10B (immunohistochemistry), skeletal muscles from exercised animals administered a control IgG antibody showed increased collagen III levels. In contrast, exercised mdx mice administered an agent that inhibits CTGF showed reduced collagen III levels as compared to that observed in animals administered a control IgG antibody (see FIGS. 9A and 9B, and FIGS. 10C and 10D).

Taken together, skeletal muscles from exercised animals administered a control IgG antibody showed increased extracellular matrix protein levels: fibronectin (see FIGS. 7A, 7B and 8A-D) and collagen III (see FIGS. 9A, 9B and 10A-D) indicating an increase in muscle fibrosis. Muscle fibrosis in exercised mdx animals administered an agent that inhibits CTGF, however, was reduced as shown by a reduction in extracellular matrix protein levels (see FIGS. 7A, 7B, 8A-D, 9A, 9B, and 10A-D).

Figure 11:
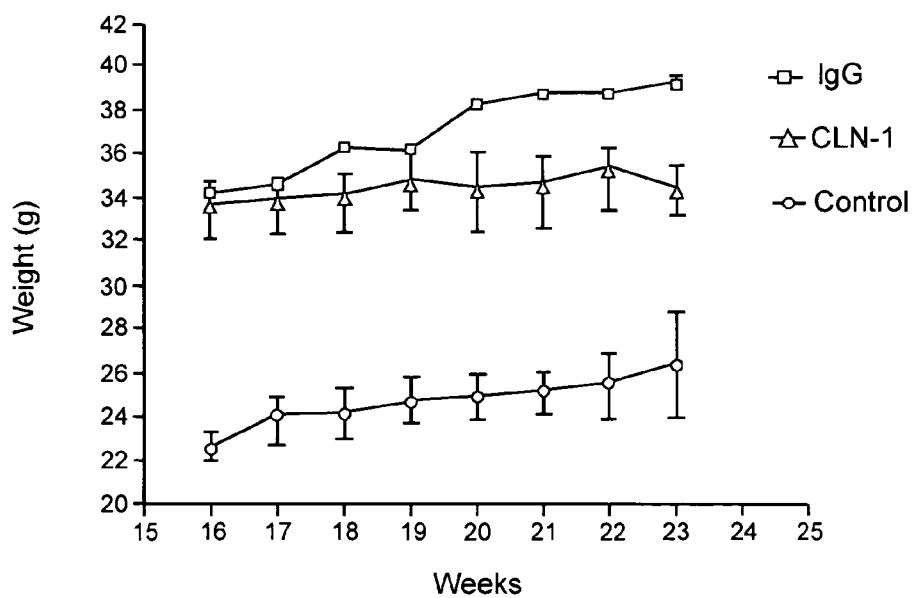
FIG. 11 sets forth data showing methods and agents of the present invention maintained bodyweight in an animal model of muscular dystrophy.

Additionally, as shown in FIG. 11, exercised mdx mice administered a control IgG antibody showed an increase in bodyweight (i.e., increased muscle damage and fibrosis) compared to that observed in healthy control mice. Bodyweight in exercised mdx animals administered an agent that inhibits CTGF, however, was maintained (see FIG. 11); indicating reduced muscle damage and fibrosis.

The results described above demonstrated that methods and agents of the present invention were effective at maintaining body weight and reducing extracellular matrix protein levels (fibronectin and collagen III) in an animal model of muscular dystrophy. Further, these results showed that methods and agents of the present invention were effective for reducing muscle fibrosis and muscle damage in an animal model of muscular dystrophy. Muscle fibrosis and muscle damage are clinical symptoms of muscular dystrophy. Therefore, these results showed that inhibition of CTGF reduced or treated clinical symptoms of muscular dystrophy. These results further suggested that inhibition of CTGF, using the methods and agents of the present invention, provides an effective treatment for muscular dystrophy.

Example 5

CTGF Inhibition Improves Muscle Function in an Animal Model of Duchenne Muscular Dystrophy The mdx mouse model of Duchenne muscular dystrophy is a model of a clinically relevant form of muscle damage and subsequent regeneration. (See Ryten et al. (2004) FASEB J. 18:1404-6.) The effect of methods and agents of the present invention on muscle function is examined using a mouse model of muscular dystrophy as follows.

Four-week old male mdx and control (C57BL/10J) mice are randomly assigned to a sedentary group or an exercise group. Exercise of the mdx mouse has been shown to accelerate muscle damage in this model (i.e. worsen the dystrophic condition). (See, e.g., De Luca et al. (2005) Am J Pathol. 166:477-89.) Mice are randomized into two treatment groups and treated as follows. Group 1 is treated with anti-CTGF antibody (CLN-1, 10 mg/kg; see International Publication No. WO 2004/108764) and Group 2 is treated with an isotype-matched control human IgG (IgG, 10 mg/kg)). Antibodies are administered i.p. at doses of 10 mg/kg (approximate injection volume of 0.5 ml) three times weekly for up to eight weeks.

The control and mdx mice in the exercised groups are subjected to 30 minutes of running on a horizontal treadmill (Columbus Instruments, USA) at 12 meters/minute, twice a week, for up to 8 weeks. (See, e.g., Luca et al. (2005)). Body weight is monitored in all animals throughout the duration of the study to assess changes in muscle mass. Blood samples are collected at various timepoints and serum creatine kinase (a marker of muscle damage) is determined for each sample using a commercial assay (Valtek, Santiago, Chile; See, e.g., Osses and Brandan (2002) Am J Physiol Cell Physiol. 282: C383-94).

After the last treatment, animals are sacrificed and their tibialis anterior and diaphragm muscles are removed for muscle function testing. Muscle function is determined by electrophysiology recordings from isometric tests in which maximal force and tetanus are measured. (See Alter et al. (2006) Nat Med. 12:175-7; Cohn et al. (2007) Nat Med. 13:204-10; Lynch et al. (2001) J Physiol. 535:591-600.) Briefly, tibialis anterior and diaphragm muscles are removed and mounted in an organ bath of Krebs solution at 36° C. (mmol/l: NaCl 113, KCl 4.7, CaCl2 1.2, MgSO4 1.2, NaHCO3 25, KH2PO4 1.2, glucose 11.5) and constantly bubbled with a mixture of 95% oxygen and 5% carbon dioxide. The initial tension is set at 20 mN; isometric contractions are measured with strain-gauge transducers and recorded on a computer. The sampling rate per channel is set at 500 Hz. The amplitude of the stimulation-evoked contractions is computed by a calculation program. After 20 minutes equilibration, electrical field stimuli are applied through two platinum wire electrodes positioned on the top and bottom of the organ bath separated by 4 cm. The muscles are stimulated with square-wave pulses of 0.25 msec duration with maximal voltage (50 V). To measure maximal force of contraction, 1 Hz stimulation is applied and the muscle twitch is recorded. To determine tetanus strength six tetanic stimulations are applied with 0.5-sec train duration at 100 Hz every 10 seconds and force measures recorded. Finally, the muscle is weighed using a microbalance. The strength measurements (i.e., maximal force and tetanus) are reported by weight unit and expressed in millinewtons per gram.

Compared to healthy control animals, exercised mdx mice administered a control IgG antibody show a reduction in maximal force and tetanus in skeletal muscle, indicating a decrease in muscle function. In contrast, exercised mdx mice administered an agent that inhibits CTGF show an increase in maximal force and tetanus in skeletal muscle compared to the values observed in muscle from animals administered control IgG antibody. These results indicate that muscle function is improved and muscle weakness is reduced by inhibition of CTGF. The results show that inhibition of CTGF improves muscle function and reduces muscle weakness in an animal model of muscular dystrophy. These results further suggest that inhibition of CTGF, using the methods and agents of the present invention, would provide an effective treatment for muscular dystrophy.

In another series of experiments, the effect of inhibition of CTGF in combination with an angiotensin receptor blocker (ARB) on muscle function is measured using an animal model of muscular dystrophy as follows. Four-week old male mdx and control (C57BL/10J) mice are randomly assigned to a sedentary group or an exercise group. Mice are randomized into four treatment groups and treated as follows. Group 1 is treated with control human IgG (10 mg/kg, IP injection, three times per week for up to 8 weeks); Group 2 is treated with anti-CTGF antibody (CLN-1, 10 mg/kg; see International Publication No. WO 2004/108764); Group 3 is treated with an ARB (Losartan 90 mg/kg/day); Group 4 is treated with anti-CTGF antibody (CLN-1, 10 mg/kg)+an ARB (Losartan 90 mg/kg/day). Antibodies are administered i.p. at doses of 10 mg/kg (approximate injection volume of 0.5 ml) three times weekly for up to eight weeks. Losartan is administered in drinking water.

The control and mdx mice in the exercised groups are subjected to 30 minutes of running on a horizontal treadmill (Columbus Instruments, USA) at 12 meters/minute, twice a week, for up to 8 weeks. (See, e.g., Luca et al. (2005)). Body weight is monitored in all animals throughout the duration of the study to assess changes in muscle mass. Blood samples are collected at various timepoints and serum creatine kinase is determined for each sample using a commercial assay (Valtek, Santiago, Chile; See, e.g., Osses and Brandan (2002) Am J Physiol Cell Physiol. 282:C383-94).

After the final administration with an agent that inhibits CTGF, animals are sacrificed and their tibialis anterior and diaphragm muscles are removed for muscle function testing. Muscle function is determined by electrophysiology recordings in which maximal force and tetanus are measured. (See Alter et al. (2006) Nat Med. 12:175-7; Cohn et al. (2007) Nat Med. 13:204-10; Lynch et al. (2001) J Physiol. 535:591-600. ) Briefly, tibialis anterior and diaphragm muscles are removed and mounted in an organ bath of Krebs solution at 36° C. (mmol/l: NaCl 113, KCl 4.7, CaCl2 1.2, MgSO4 1.2, NaHCO3 25, KH2PO4 1.2, glucose 11.5) and constantly bubbled with a mixture of 95% oxygen and 5% carbon dioxide. The initial tension is set at 20 mN; isometric contractions are measured with strain-gauge transducers and recorded on a computer. The sampling rate per channel is set at 500 Hz. The amplitude of the stimulation-evoked contractions is computed by a calculation program. After 20 minutes equilibration, electrical field stimuli are applied through two platinum wire electrodes positioned on the top and bottom of the organ bath separated by 4 cm. The muscles are stimulated with square-wave pulses of 0.25 msec duration with maximal voltage (50 V). To measure maximal force of contraction, 1 Hz stimulation is applied and the muscle twitch is recorded. To determine tetanus strength six tetanic stimulations are applied with 0.5-sec train duration at 100 Hz every 10 seconds and force measures recorded. Finally, the muscle is weighed using a microbalance. The strength measurements (i.e., maximal force and tetanus) are reported by weight unit and expressed in millinewtons per gram.

Compared to healthy control animals, exercised mdx mice administered a control IgG antibody show a reduction in maximal force and tetanus in skeletal muscle indicating a decrease in muscle function. In contrast, exercised mdx mice administered an agent that inhibits CTGF and ARB in combination show an increase in maximal force and tetanus in skeletal muscle compared to the values observed in muscle from animals administered control IgG antibody indicating that muscle function is improved by administration of an agent that inhibits CTGF in combination with ARB treatment. These results show that inhibition of CTGF in combination with ARB administration improves muscle function in an animal model of muscular dystrophy. Therefore, these results suggest that combination of an agent that inhibits CTGF and ARB therapy would provide an effective treatment for muscular dystrophy.

In one series of experiments, the effect of methods and agents of the present invention on muscle function was examined using a mouse model of muscular dystrophy as follows.

Four-month old male mdx and control (C57BL/10J) mice were used in these studies. All mice were exercised for eight weeks as described below. Mice were randomized into two treatment groups and treated as follows. Group 1 was treated with anti-CTGF antibody (CLN-1, 10 mg/kg; see International Publication No. WO 2004/108764) and Group 2 was treated with an isotype-matched control human IgG (IgG, 10 mg/kg)). Antibodies were administered i.p. at doses of 10 mg/kg (approximate injection volume of 0.5 ml) three times weekly for eight weeks.

To exercise the animals, control and mdx mice were subjected to 30 minutes of running on a horizontal treadmill (Columbus Instruments, USA) at 12 meters/minute, twice a week, for eight weeks. (See, e.g., Luca et al. (2005)). After the last treatment, animals were sacrificed and their gastrocnemius and diaphragm muscles were removed for muscle function testing.

Muscle function was determined by electrophysiology recordings from isometric tests in which maximal force and tetanus were measured. (See Alter et al. (2006) Nat Med. 12:175-7; Cohn et al. (2007) Nat Med. 13:204-10; Lynch et al. (2001) J Physiol. 535:591-600. ) Briefly, gastrocnemius and diaphragm muscles were removed and mounted in an organ bath of Krebs solution at 36° C. (mmol/l: NaCl 113, KCl 4.7, CaCl2 1.2, MgSO4 1.2, NaHCO3 25, KH2PO4 1.2, glucose 11.5) and constantly bubbled with a mixture of 95% oxygen and 5% carbon dioxide. An initial tension was set at 20 mN; isometric contractions were measured with strain-gauge transducers and recorded on a computer. The sampling rate per channel was set at 500 Hz. The amplitude of the stimulation-evoked contractions was computed by a calculation program. After 20 minutes equilibration, electrical field stimuli were applied through two platinum wire electrodes positioned on the top and bottom of the organ bath separated by 4 cm. The muscles were stimulated with square-wave pulses of 0.25 msec duration with maximal voltage (50 V). To measure maximal force of contraction, a single pulse was applied every 450 msec for 2 minutes. Muscle twitch for three pulses were recorded and the average reported. To determine tetanus strength tetanic stimulations were applied with 6 msec train duration for 1 second and force measures recorded.

The strength measurements (i.e., maximal force and tetanus) were reported by length unit and expressed in millinewtons per square millimeter.

As shown in FIGS. 12A, 12B, 12C, and 12D, compared to healthy control animals, exercised mdx mice administered a control IgG antibody showed a reduction in maximal force and tetanus in both gastrocnemius and diaphragm muscles, indicating a decrease in muscle function. In contrast, exercised mdx mice administered an agent that inhibits CTGF (CLN-1) showed an increase in maximal force and tetanus in both gastrocnemius and diaphragm muscles compared to the values observed in muscle from animals administered control IgG antibody (see FIGS. 12A-D). These results indicated that muscle function is improved and muscle weakness is reduced by inhibition of CTGF. The results also showed that inhibition of CTGF improved muscle function and reduced muscle weakness in an animal model of muscular dystrophy. These results further suggested that inhibition of CTGF, using the methods and agents of the present invention, would provide an effective treatment for muscular dystrophy.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method for increasing muscle strength in a subject having muscular dystrophy, the method comprising administering to the subject a therapeutically effective amount of an anti-connective tissue growth factor (CTGF) antibody or fragment thereof, thereby increasing muscle strength.

2. The method of claim 1, wherein muscular dystrophy is selected from the group consisting of Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

3. The method of claim 1, wherein the subject is human.

4. The method of claim 1, wherein the anti-CTGF antibody is a monoclonal antibody or a fragment thereof.

5. The method of claim 4, wherein the anti-CTGF monoclonal antibody is CLN-1, or a fragment thereof.

6. The method of claim 1, further comprising administering an angiotensin receptor blocker, a statin, a calcium channel blocker, a beta-blocker, a glucocorticoid, an advanced glycation endproduct inhibitor or a diuretic.

7. A method for increasing the maximal force or tetanus strength of muscle in a subject having muscular dystrophy, the method comprising administering to the subject a therapeutically effective amount of an anti-CTGF antibody or fragment thereof, thereby increasing the maximal force or tetanus strength of muscle.

8. The method of claim 7, wherein muscular dystrophy is selected from the group consisting of Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

9. The method of claim 7, wherein the subject is human.

10. The method of claim 7, wherein the anti-CTGF antibody is a monoclonal antibody or a fragment thereof.

11. The method of claim 10, wherein the anti-CTGF monoclonal antibody is CLN-1, or a fragment thereof.

12. The method of claim 7, further comprising administering an angiotensin receptor blocker, a statin, a calcium channel blocker, a beta-blocker, a glucocorticoid, an advanced glycation endproduct inhibitor or a diuretic.

* * * * *